(12) United States Patent
Hu et al.

(10) Patent No.: US 10,060,930 B2
(45) Date of Patent: *Aug. 28, 2018

(54) SYSTEMS AND METHODS FOR CHARACTERIZING KIDNEY DISEASES

(71) Applicant: Renovar Incorporated, Atlanta, GA (US)

(72) Inventors: Huaizhong Hu, Madison, WI (US); Stuart Knechtle, Atlanta, GA (US)

(73) Assignee: Renovar Incorporated, Atlanta, GA (US)

( * ) Notice: Subject to any disclaimer, the term of this patent is extended or adjusted under 35 U.S.C. 154(b) by 214 days.

This patent is subject to a terminal disclaimer.

(21) Appl. No.: 14/987,274

(22) Filed: Jan. 4, 2016

(65) Prior Publication Data

US 2016/0116484 A1 Apr. 28, 2016

Related U.S. Application Data

(63) Continuation of application No. 13/452,569, filed on Apr. 20, 2012, now Pat. No. 9,229,011, which is a continuation of application No. 12/330,239, filed on Dec. 8, 2008, now abandoned, which is a continuation of application No. 11/602,530, filed on Nov. 21, 2006, now Pat. No. 7,476,497, which is a continuation of application No. 11/010,685, filed on Dec. 13, 2004, now Pat. No. 7,138,230, which is a continuation-in-part of application No. 10/903,797, filed on Jul. 30, 2004, now Pat. No. 7,138,229, which is a continuation-in-part of application No. 10/313,807, filed on Dec. 6, 2002, now Pat. No. 7,244,555.

(60) Provisional application No. 60/499,937, filed on Sep. 3, 2003, provisional application No. 60/491,900, filed on Aug. 1, 2003, provisional application No. 60/380,569, filed on May 14, 2002.

(51) Int. Cl.
*G01N 33/68* (2006.01)
*G01N 33/574* (2006.01)

(52) U.S. Cl.
CPC ... *G01N 33/6863* (2013.01); *G01N 33/57442* (2013.01); *G01N 33/6893* (2013.01); *G01N 2333/522* (2013.01); *G01N 2333/70578* (2013.01); *G01N 2333/715* (2013.01); *G01N 2800/245* (2013.01); *G01N 2800/347* (2013.01); *G01N 2800/60* (2013.01)

(58) Field of Classification Search
CPC ......... G01N 33/6863; G01N 33/57442; G01N 33/6893
See application file for complete search history.

(56) References Cited

U.S. PATENT DOCUMENTS

| 5,484,707 | A | 1/1996 | Goldblum et al. |
| 2003/0215886 | A1 | 11/2003 | Hu |
| 2005/0112688 | A1 | 5/2005 | Hu |
| 2005/0158801 | A1 | 7/2005 | Hu |

FOREIGN PATENT DOCUMENTS

| WO | 200178708 | 10/2001 |
| WO | 2003098185 | 11/2003 |
| WO | 2005012907 | 1/2005 |
| WO | 2005002416 | 10/2005 |

OTHER PUBLICATIONS

U.S. Appl. No. 10/903,797, filed May 26, 2005, Huaizhong Hu, et al.
U.S. Appl. No. 10/313,807, filed Feb. 6, 2002, Huaizhong Hu, et al.
Malyszko et al: "Osteoprotegerin and its correlations with new markers of bone formation and bone resorption in kidney transplant recipients," Transplantation Proceedings, Orlando, FL, US, vol. 35, No. 6. Sep. 1, 2003 (Sep. 1, 2003), pp. 2227-2229, XP005160889 ISSN: 0041-1345.
Kazama J J et al: "Increased circulating levels of osteoclastogenesis inhibitory factor (osteoprotegerin) in patients with chronic renal failure," American Journal of Kidney Diseases 2002 US, vol. 39, No. 3, 2002, pp. 525-532, ISSN: 0272-6386.
Sato T et al: "Osteoprotegerin levels before and after renal transplantation," American Journal of Kidney Diseases: The Official Journal of the National Kidney Foundation, Oct. 2001, vol. 38, No. 4 Suppl 1, Oct. 2001 (Oct. 2001), pp. S175-S177, ISSN: 1523-6838.
Moreb Jans S, et al, "Monitoring serum and urine osteoprotegrin levens during the treatment of patients with multiple myeloma," Blood, Nov. 16, 2003, p. 374b, Ann Meeting of the American Society of Hematology; vol. 102 No. 11, San Diego CA USA.
Zhu H, Snyder M; "Protein chip technology," Current Opinion in Chemical Biology, 2003, vol. 7, p. 55-63.
Cutler P, "Protein arrays: The current state of the art," Proteomics, 2003 vol. 3, pp. 3-18.
Koehler, "Continuous culture of fused cells secreting antibody of predefined specificity," Nature, 1975, vol. 256, p. 495.
Hu et al. "Elevation of CXCR3-Binding Chemokines in Urine Indicates Acute Renal-Allograft Dysfunction," American J. Transol. 2004' 4:432-437.
Segerer et al. "Chemokines, Chemokine Receptors, and Renal Disease: From Basic Science to Pathophysiologic and Therapeutic Studies," J. Am. Soc. Nephrol. 2000, 11:152-176'.
Nelson et al. "Chemokines, Chemokine Receptors, and Allograft Rejection," Immunity. 2001, 14:377-386 April.

(Continued)

*Primary Examiner* — Taeyoon Kim
*Assistant Examiner* — Tiffany M Gough
(74) *Attorney, Agent, or Firm* — Casimir Jones, S.C.; David Casimir

(57) ABSTRACT

The present invention relates to methods of diagnosing, predicting and monitoring kidney disorders. In particular, the present invention relates to the diagnosis, prediction and monitoring of kidney disorders by detection of cytokines, cytokine-related compounds and chemokines in urine. The present invention further relates to methods and compositions for assessing the efficacy of agents and interventions used to treat kidney disorders.

7 Claims, 12 Drawing Sheets

(56) References Cited

OTHER PUBLICATIONS

Romagnani el al. "Role for Interactions Between IP-10/Mig and CXCR2 in Proliferative Glomerulonephritis," J Am Soc Nephrol. Dec. 1999—10(12) :2518-26.
Gao, Transplantation "Beneficial Effects of Targeting CCR5 in Allograft Recipients" Oct. 72(7):1199-1205, 2001.
Raybiotech. Inc. RayBio Cytokine Antibody Array web based product literature.
Upstate Cell Signaling Solutions, Beadlyte, Kits and Reagents for Luminex, Detection Systems web based product literature Kils.
Hancock et al., J. Exp Med. "Requirement of the Chemokine Receptor CXCR3 for Acute Allograft Rejection" Nov. 192(10):1515-20. 2000.
Gerard et al., Nat. Immunol. "Chemokines and disease" Feb. 2(2):108-15. 2001.
Wong et al., Curr. Opin. Nephrol. Hypertens. "Urinary cytokines: clinically useful markers of chronic renal disease progression?" Nov; 10(6):807-11. 2001.
Maier et al., Shock "Massive chemoldnetranscription in acute renal failure due to polymicrobial sepsis." Aug; 14(2):187-92. 2000 (abstract only).
Poppas et al., Urology "Intravesical bacille Calmette-Guerin induces the antiangiogenic chemokine interferon. inducible protein 10" Aug. 1998; 52(2):268-75; discussion 275-6.
Rovin et al., Am. J. Kidney Dis. "Monocyte chemoattractant protein-1 levels in patients with glomerular disease." May 1996;27(5):640-6. (abstract only).
Olszyna et al., "Sequential measurements of chemokines in urosepsis and experimental endotoxemia." J Clin Immunol. Nov. 1999; 19(6):399-405. (abstract only).
Kacprzyk "Serum level and urinary excretion of RANTES in patients with primary glomerulonephritis" Pol Arch Med Wewn. Sep. 2002; 108(3):837-42. (abstract only).
Sibbring: et at "Localization for C-X-C chemokines to renal tubular epithelial cells in human kidney transplants is not =fined to acute cellular rejection," Transpl Immunol. Dec. 1998—6(4):203.8 (Abstract Only).
Pattison et al., "RANTES chemokine expression in cell-mediated transplant rejection of the kidney" Lancet. Jan. 22, 1994;343(8891):209-11. (abstract only).
Segerer et al., "Expression of the C-C chemokine receptor 5 in human kidney diseases" Kidney Int. Jul. 1999;56(1):52-64. (abstract only).
Grandaliano et al., "Monocyte chemotactic peptide-1 expression and monocyte infiltration in acute renal transplant rejection." Transplantation. Feb. 15, 1997;63(3):414-20. (abstract only).
Yun et al., "Early and late chemokine production correlates with cellular recruitment in cardiac allograft vasculopathy" Transplantation. Jun. 27, 2000;69(12):2515-24. (abstract only).
Segerer et al., "Expression of Chemokines and Chemokine Receptors During Human Renal Transplant Rejection" American Journal ofKidney Diseases, Vo137, No. 3 Mar. 2001: pp. 518-531.
Hancock. "Chemokines and Transplant. Immunobiology." J Am See Nephrol 13: 821-824, 2002.
Afrouzian et al., "Transcription Factor IRF-1 in Kidney Transplants Mediates Resistance to :Graft Necrosis during Rejection" J Am Soc Nephrol 13: 1199-1209, 2002.
Romagnani et al., "High expression of chemokines intereron-gamma Inducible protein of 10kDa(IP-10), Monokines induced by interferon-y (MIG) and of their receptor (CXCR3) in acute renal rejection" Am J Transplant, vol. S343, Abstract #825 (2001).
Inston et al., "The revolving role of chemokines and their receptors in acute allograft rejection," Nephrol Dial Transplant (2002) 17:1374-1379.
Loetscher et al., "Chemokine Receptor Specific for IP10 and Mig: Structure, Function, and Expression in Activated T-Lymphocytes," J Exp Med vol. 184 Sep. 1996, 963-969.
Wada et al., "Chemokines: New Target Molecules in Renal Diseases," Clinical and Experimental Nephrology 4(4):273, 2000 (Abstract Only).
Schindler et al., "Renal problems after lung transplantation of cystic fibrosis patients," Nephrol Dial Transplant, (2001) V. 16, pp. 1324-1338.
Sanchez et al., "Preoperative and perioperative predictors of the need for renal replacement therapy after orthotopic liver transplantation," Transplantation, (Oct. 25, 2004) vol. 7, No. 7, pp. 1048-1054.

Figure 3.

| | acute rejection (n=28) | suspicious acute rejection (n=9) | BK virus nephritis (n=6) | acute tubular injury (n=10) | chronic rejection (n=20) | stable graft function (n=26) | healthy control (n=16) |
|---|---|---|---|---|---|---|---|
| IP-10 | 25 (89.3%) | 4 (44.4%) | 6 (100%) | 7 (70.0%) | 2 (10.0%) | 2 (7.6%) | 0 (0%) |
| Mig | 21 (75%) | 3 (33.3%) | 6 (100%) | 8 (80.0%) | 2 (10.0%) | 1 (3.8%) | 0 (0%) |
| I-TAC | 10 (35.7%) | 0 (0%) | 2 (33.3%) | 3 (30.0%) | 0 (0%) | 0 (0%) | 0 (0%) |
| IP-10+Mig | 25 (89.3%) | 4 (44.4%) | 6 (100%) | 8 (80.0%) | 4 (20.0%) | 2 (7.6%) | 0 (0%) |

Figure 4.

|               | Sensitivity (%) | Specificity (%) | Positive predictive value (%) | Negative predictive value (%) |
|---------------|-----------------|-----------------|-------------------------------|-------------------------------|
| IP-10         | 86.4            | 91.3            | 90.5                          | 87.5                          |
| Mig           | 79.5            | 93.5            | 92.1                          | 82.7                          |
| IP-10 and Mig | 88.6            | 87.0            | 86.6                          | 88.9                          |

Day after diagnosis of acute rejection

Day after initiation of anti-rejection therapy

Figure 8
Screening urinary samples with a microarray consisting of cytokines and chemokines

| | Acute Rejection (n=5) | Acute Tubular Necrosis (n=5) | Chronic Allograft Nephropathy (n=8) | Stable Grafts (n=10) | Healthy Controls (n=6) |
|---|---|---|---|---|---|
| | | Mean ± SD (Range) | | | |
| Group I | | | | | |
| Angiogenin | 101.4 ± 49.0 (44.1-167.9) | 196.6 ± 88.3 (122.2-306.2) | 137.6 ± 98.8 (39.0-303.3) | 92.9 ± 51.5 (3.0-173.9) | 100.5 ± 69.8 (7.9-171.3) |
| TIMP-2 | 150.5 ± 90.9 (34.3-276.4) | 223.1 ± 194.7 (45.9-538.6) | 260.8 ± 370.4 (12.8-1084.3) | 177.4 ± 390.8 (2.5-1282.7) | 139.8 ± 108.5 (13.3-289.7) |
| TNF sR2 | 292.7 ± 44.8 (229.7-355.4) | 294.4 ± 16.2 (276.9-319.2) | 264.5 ± 45.7 (195.3-301.1) | 232.7 ± 91.7 (40.0-325.7) | 148.4 ± 101.1 (24.5-285.8) |
| TRAIL R3 | 33.0 ± 5.1 (28.8-41.4) | 33.0 ± 14.7 (13.1-48.6) | 25.6 ± 11.7 (14.9-49.7) | 46.6 ± 21.6 (10.2-73.8) | 52.1 ± 27.6 (8.1-80.4) |
| Group II | | | | | |
| IL-1β | 1.5 ± 1.5 (0.6-4.1) | 1.3 ± 0.2 (1.0-1.6) | 1.4 ± 0.9 (0.3-3.1) | 28.4 ± 83.7 (0.7-266.6) | 1.3 ± 0.6 (0.7-2.1) |
| IL-2sRα | 0.5 ± 0.3 (0.0-0.7) | 0.4 ± 0.1 (0.3-0.6) | 0.6 ± 0.2 (0.1-0.8) | 0.6 ± 0.2 (0.2-1.1) | 0.6 ± 0.2 (0.3-0.9) |
| IL-6 | 0.8 ± 0.5 (0.2-1.6) | 0.9 ± 0.7 (0.4-2.1) | 0.7 ± 0.5 (0.2-1.4) | 0.9 ± 0.7 (0.2-2.9) | 0.8 ± 0.3 (0.6-1.3) |
| MIP-1α | 0.6 ± 0.1 (0.5-0.7) | 0.6 ± 0.2 (0.4-0.9) | 0.7 ± 0.2 (0.4-1.1) | 0.8 ± 0.1 (0.6-1.0) | 0.9 ± 0.2 (0.6-1.1) |
| MIP-1β | 0.8 ± 0.5 (0.1-1.3) | 1.0 ± 0.7 (0.4-2.0) | 0.9 ± 0.2 (0.5-1.2) | 0.9 ± 0.5 (0.1-1.5) | 0.9 ± 0.3 (0.4-1.2) |
| MIP-3α | 1.3 ± 1.6 (0.3-4.2) | 2.9 ± 3.8 (0.3-9.6) | 1.5 ± 2.4 (0.1-7.4) | 1.1 ± 0.5 (0.3-1.8) | 1.0 ± 0.3 (0.5-1.2) |
| IL-18 | 2.1 ± 0.9 (1.0-3.4) | 2.5 ± 0.6 (1.6-3.4) | 1.3 ± 0.7 (0.6-2.8) | 1.4 ± 0.5 (0.8-2.3) | 1.0 ± 0.3 (0.8-1.5) |
| TNF-α | 5.1 ± 5.1 (1.2-13.5) | 2.2 ± 1.0 (0.7-3.3) | 3.1 ± 2.5 (1.1-8.8) | 3.5 ± 2.6 (0.6-8.1) | 2.6 ± 1.2 (1.7-4.8) |
| Group III | | | | | |
| Adiponectin | 10.0 ± 5.3 (2.3-14.4) | 18.0 ± 10.2 (6.0-33.4) | 16.0 ± 9.3 (7.2-30.2) | 13.4 ± 15.7 (1.3-52.5) | 2.4 ± 1.4 (0.8-4.2) |
| IGFBP1 | 12.4 ± 10.0 (2.0-28.5) | 37.6 ± 20.2 (13.3-60.0) | 27.2 ± 15.0 (4.9-46.2) | 12.6 ± 21.2 (0.9-57.1) | 2.4 ± 0.9 (1.7-4.1) |
| IGFBP-2 | 31.8 ± 42.6 (10.8-108.0) | 109.4 ± 92.1 (34.3-244.3) | 53.8 ± 48.4 (3.9-124.9) | 18.3 ± 22.0 (0.7-62.1) | 5.0 ± 3.9 (0.8-11.8) |
| IGFBP-6 | 71.6 ± 69.3 (2.5-177.5) | 124.5 ± 85.5 (23.9-207.6) | 90.6 ± 67.1 (8.5-190.2) | 33.7 ± 56.4 (0.6-160.6) | 2.5 ± 0.6 (1.8-3.4) |
| IL-8 | 3.2 ± 3.2 (1.3-8.8) | 10.6 ± 10.5 (2.3-27.5) | 3.5 ± 1.9 (1.4-7.1) | 20.8 ± 57.7 (0.8-184.9) | 2.5 ± 0.9 (1.3-3.7) |
| Leptin | 40.1 ± 65.6 (0.4-151.8) | 8.0 ± 9.2 (0.2-22.6) | 1.3 ± 1.3 (0.5-4.4) | 1.0 ± 0.4 (0.5-1.8) | 0.7 ± 0.1 (0.6-0.9) |
| MCP-1 | 19.9 ± 19.7 (2.0-52.0) | 24.3 ± 29.5 (1.9-75.5) | 10.7 ± 7.1 (2.4-19.6) | 2.5 ± 1.6 (0.7-6.3) | 1.8 ± 0.9 (1.0-3.4) |
| MIP-1δ | 59.0 ± 115.3 (2.6-264.8) | 64.8 ± 64.8 (11.5-169.0) | 39.5 ± 57.5 (2.3-152.3) | 6.3 ± 6.8 (1.1-24.2) | 2.0 ± 0.7 (1.2-2.8) |
| TNF sR1 | 400.9 ± 246.9 (44.0-731.1) | 416.4 ± 257.4 (129.0-699.2) | 350.1 ± 224.3 (89.5-631.8) | 192.0 ± 221.8 (5.9-628.7) | 18.1 ± 11.6 (3.1-34.4) |
| Osteoprotogerin | 32.2 ± 35.8 (8.6-95.7) | 97.9 ± 122.4 (20.8-313.9) | 44.8 ± 32.5 (8.1-90.7) | 25.9 ± 28.7 (2.0-70.5) | 7.5 ± 4.9 (1.1-13.1) |
| uPAR | 148.5 ± 80.8 (27.5-252.2) | 167.3 ± 95.1 (98.9-333.0) | 108.0 ± 99.9 (24.0-331.0) | 63.0 ± 74.6 (4.3-255.2) | 11.8 ± 7.1 (2.7-18.2) |

Figure 11

Kidney graft recipients and healthy individuals with the urinary levels of chemokines and OPG above 80.0 pg/ml

| | AR (n=37) | Borderline (n=10) | ABAR (n=4) | ATN (n=9) | BKVN (n=4) | CAN (n=20) | SGF (n=29) | HC (n=19) |
|---|---|---|---|---|---|---|---|---|
| IP-10 (Pg/ml) | 35 (94.6%) | 6 (60.0%) | 3 | 6 (66.7%) | 4 | 9 (45.0%) | 3 (10.3%) | 1 (5.3%) |
| Mig (pg/ml) | 32 (86.5%) | 5 (50.0%) | 3 | 7 (77.8%) | 4 | 3 (15.0%) | 3 (10.3%) | 1 (5.3%) |
| MIP-1δ (pg/ml) | 33 (89.2%) | 9 (90.0%) | 4 | 7 (77.8%) | 3 | 20 (100.0%) | 8 (27.6%) | 0 (0.0%) |
| OPG (pg/ml) | 22 (59.5%) | 7 (70.0%) | 3 | 5 (55.6%) | 2 | 10 (50.0%) | 5 (17.2%) | 0 (0.0%) |

Figure 12

| | Sensitivity (%) | Specificity (%) | Positive Predictive Value (%) | Negative predictive Value (%) |
|---|---|---|---|---|
| IP-10 | 88.9 | 80.9 | 78.7 | 90.2 |
| Mig | 85.2 | 89.7 | 86.8 | 88.4 |
| MIP-1d | 90.5 | 83.3 | 90.5 | 83.3 |
| Osteoprotogerin | 58.3 | 89.6 | 90.7 | 55.1 |

SYSTEMS AND METHODS FOR CHARACTERIZING KIDNEY DISEASES

The present application is a continuation of U.S. application Ser. No. 13/452,569, filed Apr. 20, 2012, which is a continuation of U.S. application Ser. No. 12/330,239, filed Dec. 8, 2008, now abandoned, which is a continuation of U.S. application Ser. No. 11/602,530, filed Nov. 21, 2006, now U.S. Pat. No. 7,476,497, which is a continuation of U.S. application Ser. No. 11/010,685 filed Dec. 13, 2004, now U.S. Pat. No. 7,138,230, which is a continuation-in-part of U.S. application Ser. No. 10/903,797, filed Jul. 30, 2004, now U.S. Pat. No. 7,138,229, which claims priority to U.S. Provisional application Ser. No. 60/491,900 filed Aug. 1, 2003, and 60/499,937, filed Sep. 3, 2003, and is also a continuation-in-part of U.S. application Ser. No. 10/313,807, filed Dec. 6, 2002, now U.S. Pat. No. 7,244,555, which claims priority to U.S. Provisional application Ser. No. 60/380,569, filed May 14, 2002, each of which is incorporated herein by reference in its entirety.

FIELD OF THE INVENTION

The present invention relates to methods of diagnosing, predicting and monitoring kidney disorders. In particular, the present invention relates to the diagnosis, prediction and monitoring of kidney disorders by detection of cytokines, cytokine-related compounds, and chemokines in urine. The present invention further relates to methods and compositions for assessing the efficacy of agents and interventions used to treat kidney disorders.

BACKGROUND OF THE INVENTION

The diagnosis of kidney disorders is classically based on the presence of one or more signs and symptoms. For example, signs and symptoms of acute renal failure, renal tubular injury, renal cancer or glomerulonephritis may include weight gain, reduced urine output, increased serum creatine concentrations, hypertension, fever, and kidney enlargement and tenderness. However, the use of these signs and symptoms alone to detect kidney disorders is not adequate. Currently, most kidney disorders are diagnosed by measuring kidney function, for example by using biochemical tests such as assays that measure serum creatinine (Cr) concentrations, and by imaging or biopsy.

Presently, renal biopsy remains the most definitive test to specifically diagnose many kidney disorders. However, renal biopsy has major limitations. For example, the biopsy procedure itself has complications, and cannot be performed on a routine or serial basis to monitor progression of renal disease. In addition, a renal biopsy is invasive, making it uncomfortable, inconvenient and often dangerous for patients. Moreover, accurate interpretation of a renal biopsy demands the expertise of a pathologist with extensive experience in analyzing the sample for evidence of specific kidney disorders. Hence, renal biopsies are reserved for those patients demonstrating other clinical and/or laboratory evidence of a kidney disorders, thus limiting its broader use.

Thus, a less invasive method for the diagnosis, prediction and monitoring of kidney disorder is clearly needed.

SUMMARY OF THE INVENTION

The present invention relates to methods of diagnosing, predicting and monitoring kidney disorders. In particular, the present invention relates to the diagnosis, prediction and monitoring of kidney disorders by detection of cytokines, cytokine-related compounds or chemokines in urine, or in other body fluids, for example, blood, serum, plasma, bile, saliva, or cerebrospinal fluid. The present invention further relates to methods and compositions for assessing the efficacy of agents and interventions used to treat kidney disorders.

Accordingly, in some embodiments, the present invention provides a method for diagnosing disorders of the kidney comprising providing a urine sample from a subject, wherein said subject is suspected of having a kidney disorder, providing reagents for detection of at least one compound from the list comprising adiponectin, IGFBP-1, IGFBP-2, IGFBP-6, IL-8, leptin, MCP-1, MIP-1$\delta$, TNF sR1, osteoprotogerin, and uPAR, and detecting the presence of said compound in said urine sample using said reagents. In some embodiments, said list of said compounds further comprises IP-10 and Mig. In other embodiments, said detecting the presence of said compound in said urine sample comprises detecting the amount of said compound in said urine sample. In other embodiments, said method further comprises providing a sample additive composition comprising a high concentration salt buffer, wherein said salt buffer, when mixed with an equal volume of urine and said reagents for detection, provides a concentration of said salt of 200-600 mM in said mixture.

In some embodiments, said compound is a full size compound. In other embodiments said compound is a fragment of said full size compound. In further embodiments, said reagents comprise reagents for performing an immunoassay. In preferred embodiments said immunoassay is selected from the group comprising an ELISA, radio-immunoassay, automated immunoassay, cytometric bead assay, and immunoprecipitation assay. In other embodiments, said reagents comprise reagents for performing a fluorescently activated cell sorting assay. In some embodiments, the present invention further comprises the step of determining a treatment course of action based on said diagnosis of a kidney disorder. In other embodiments, the present invention further comprises the step of determining the presence or absence of a concurrent infection in said subject.

The present invention further provides a method of diagnosing a kidney disorder, comprising providing a urine sample from a subject, providing reagents for detection of two or more compounds from the list comprising adiponectin, IGFBP-1, IGFBP-2, IGFBP-6, IL-8, leptin, MCP-1, MIP-1$\delta$, TNF sR1, osteoprotogerin, and uPAR, detecting the presence of said two or more compounds from said list, and diagnosing a kidney disorder in said subject based on the result of said detecting. In some embodiments, said list of said compounds further comprises IP-10 and Mig. In other embodiments, said detecting the presence of said compound in said urine sample comprises detecting the amount of said compound in said urine sample. In some embodiments, said method further comprises the step of determining a treatment course of action based on said diagnosis of a kidney disorder. In other embodiments said method further comprises the step of determining the presence or absence of a concurrent infection in said subject.

The present invention additionally provides a method for distinguishing acute renal graft rejection from chronic renal graft rejection, comprising providing a urine sample from a subject, wherein said subject is suspected of having renal graft rejection, and reagents for detection of at least one cytokine, cytokine-related compound or chemokine, and detecting the presence of said cytokine, cytokine-related compound or chemokine in said urine sample using said reagents. In some embodiments, said detecting the presence of said cytokine compound in said urine sample comprises detecting the amount of said cytokine compound in said urine sample.

In further embodiments, the present invention provides a kit, comprising reagents for the detection of the amount one or more compounds selected from the list comprising adiponectin, IGFBP-1, IGFBP-2, IGFBP-6, IL-8, leptin, MCP-1, MIP-1δ, TNF sR1, osteoprotogerin, and uPAR, instructions for using said reagents for detecting the presence of one or more of said compounds, and instructions for using said detecting the presence of said one or more compounds in said urine sample for diagnosing a kidney disorder. In some embodiments, said list of said compounds further comprises IP-10 and Mig. In other embodiments, said detecting the presence of said compound in said urine sample comprises detecting the amount of said compound in said urine sample. In further embodiments, said kit further comprises a sample additive composition comprising a high concentration salt buffer, wherein said salt buffer, when mixed with an equal volume of urine and said reagents for detection, provides a concentration of said salt of 200-600 mM in said mixture. In some embodiments, said instructions comprise instructions required by the United States Food and Drug Administration for use in in vitro diagnostic products. In still further embodiments, said kit further comprises second reagents for determining the presence or absence of a concurrent infection in said subject, and second instructions for using said reagents for determining the presence or absence of said concurrent infection in said subject.

In some embodiments, the present invention provides a method of detecting kidney disease markers, comprising providing a urine sample from a subject, wherein said subject is suspected of having acute renal failure, renal tubular interstitial disease or glomerulonephritis; reagents for detection of a CXCR3 ligand or CCR-5 receptor ligand (e.g., CCL chemokines); and detecting the presence of said ligand in said urine sample using said reagents. In some embodiments, the method further provides the step of predicting renal failure risk in the subject based on the result of the detecting. In other embodiments, the method further provides the step of detecting renal failure risk in the subject based on the result of the detecting. In some embodiments, detecting the presence of the ligand in the urine sample comprises detecting the amount of the ligand in the urine sample. The present invention is not limited to the detection of a particular ligand. Any suitable ligand is contemplated including, but not limited to, IP-10, Mig, I-TAC, MIP-1α, MIP-3α, and MIP-1β. In some embodiments, the ligand is a full length ligand. In other embodiments, the ligand is a fragment of the full length ligand. The present invention is not limited to a particular assay. In some embodiments, the reagents comprise reagents for performing an immunoassay. For example, any suitable immunoassay is contemplated including, but not limited to, ELISA, radio-immunoassay, automated immunoassay, cytometric bead assay, and immunoprecipitation assay. In some embodiments, the ELISA is a quantitative ELISA assay. In other embodiments the assay is a Luminex bead assay. In further embodiments, the assay is a protein microarray. In some embodiments, the present invention further comprises the step of determining a treatment course of action based on the prediction of acute renal failure, tubular interstitial disease or glomerulonephritis risk. In some embodiments, the treatment course of action comprises the administration of therapeutic agents. In some embodiments, the treatment course of action comprises a surgical procedure. In additional embodiments the surgical procedure comprises renal transplantation. In further embodiments the treatment course of action comprises dialysis. In some embodiments the dialysis is hemodialysis. In other embodiments the dialysis is peritoneal dialysis. In other embodiments, the treatment course of action comprises continued monitoring. In some embodiments, the present invention further comprises the step of determining the presence or absence of a concurrent infection in the subject. In some embodiments, the determining of a concurrent infection comprises determining the body temperature of the subject. In other embodiments, the determining of a concurrent infection comprises the detection of a bacterial infection in the subject. In still further embodiments, the determining of a concurrent infection comprises the detection of a viral infection in the subject.

The present invention further provides a method of diagnosing acute renal failure, tubular interstitial disease, renal cancer or glomerulonephritis in a subject, comprising providing a urine sample from a subject; reagents for detection of a CXCR3 ligand or CCR-5 receptor ligand (e.g., CCL chemokines); and detecting the presence of the ligand in the urine sample using the reagents; and diagnosing acute renal failure, tubular interstitial disease, renal cancer or glomerulonephritis in the subject based on the result of the detecting. In some embodiments, detecting the presence of the ligand in the urine sample comprises detecting the amount of the ligand in the urine sample. The present invention is not limited to the detection of a particular ligand. Any suitable ligand is contemplated including, but not limited to, IP-10, Mig, I-TAC, MIP-1α, MIP-3α, and MIP-1β. In some embodiments, the ligand is a full-length ligand. In other embodiments, the ligand is a fragment of the full length ligand. The present invention is not limited to a particular assay. In some embodiments, the reagents comprise reagents for performing an immunoassay. For example, any suitable immunoassay is contemplated including, but not limited to, ELISA, radio-immunoassay, automated immunoassay, cytometric bead assay, and immunoprecipitation assay. In some embodiments, the ELISA is a quantitative ELISA assay. In other embodiments the assay is a Luminex bead assay. In further embodiments, the assay is a protein microarray. In some embodiments, the method further comprises the step of determining a treatment course of action based on the diagnosis of acute renal failure, tubular interstitial disease or glomerulonephritis. In some embodiments, the present invention further comprises the step of determining the presence or absence of a concurrent infection in the subject. In some embodiments, the determining of a concurrent infection comprises determining the body temperature of the subject. In other embodiments, the determining of a concurrent infection comprises the detection of a bacterial infection in the subject. In still further embodiments, the determining of a concurrent infection comprises the detection of a viral infection in the subject.

The present invention additionally provides a method of determining a treatment course of action, comprising providing a urine sample from a subject, wherein the subject is suspected of having acute renal failure, tubular interstitial disease, renal cancer or glomerulonephritis for detection of a chemokine; and detecting the amount of the chemokine in the urine sample using the reagents; and determining a treatment course of action based on the detecting. In some embodiments, the treatment course of action comprises continued monitoring. In some embodiments, the chemokine comprises a CXCR3 ligand or a CCL chemokine. The present invention is not limited to the detection of a particular ligand. Any suitable ligand is contemplated including, but not limited to, IP-10, Mig, I-TAC, MIP-1α, MIP-3α, and MIP-1β. In some embodiments, the ligand is a full-length ligand. In other embodiments, the ligand is a fragment of a full-length ligand. The present invention is not limited to a particular assay. In some embodiments, the reagents comprise reagents for performing an immunoassay. For example, any suitable immunoassay is contemplated including, but not limited to, ELISA, radio-immunoassay, automated immunoassay, cytometric bead assay, and immunoprecipitation assay. In some embodiments, the ELISA is a quantitative ELISA assay. In other embodiments the assay is a Luminex bead assay. In further embodiments, the assay is a protein microarray. In some embodiments, the present invention further comprises the step of determining a treatment course of action based on the prediction of acute renal failure, tubular interstitial disease or glomerulonephritis risk. In some embodiments, the treatment course of action comprises the administration of therapeutic agents. In some embodiments, the treatment course of action comprises a surgical procedure. In additional embodiments the surgical procedure comprises renal transplantation. In further embodiments the treatment course of action comprises dialysis. In some embodiments the dialysis is hemodialysis. In other embodiments the dialysis is peritoneal dialysis. In some embodiments, the present invention further comprises the step of determining the presence or absence of a concurrent infection in the subject. In some embodiments, the determining of a concurrent infection comprises determining the body temperature of the subject. In other embodiments, the determining of a concurrent infection comprises the detection of a bacterial infection in the subject. In still further embodiments, the determining of a concurrent infection comprises the detection of a viral infection in the subject.

The present invention also provides a method of screening compounds, comprising providing a sample from a subject, wherein the subject is suspected of having acute renal failure, tubular interstitial disease or glomerulonephritis; an assay with reagents for detection of a CXCR3 ligand or CCR-5 receptor ligand (e.g., CCL chemokines); and one or more test compounds; and administering the test compound to the subject; detecting the amount of the ligand in the sample using the reagents. The present invention is not limited to a particular sample type. Any bodily fluid including, but not limited to, blood, urine, serum, and lymph may be utilized. In some preferred embodiments, the sample is a urine sample. In some embodiments, the test compound is a drug. In some embodiments, the method further comprises the step of determining the efficacy of the drug based on the detecting. The present invention is not limited to the detection of a particular ligand. Any suitable ligand is contemplated including, but not limited to, IP-10, Mig, I-TAC, MIP-1α, MIP-3α, and MIP-1β. In some embodiments, the ligand is a full-length ligand. In other embodiments, the ligand is a fragment of a full-length ligand. The present invention is not limited to a particular assay. In some embodiments, the reagents comprise reagents for performing an immunoassay. For example, any suitable immunoassay is contemplated including, but not limited to, ELISA, radio-immunoassay, automated immunoassay, cytometric bead assay, and immunoprecipitation assay. In some embodiments, the ELISA is a quantitative ELISA assay. In other embodiments the assay is a Luminex bead assay. In further embodiments, the assay is a protein microarray. In some embodiments, the present invention further comprises the step of determining the presence or absence of a current infection in the subject. In some embodiments, the determining of a concurrent infection comprises determining the body temperature of the subject. In other embodiments, the determining of a concurrent infection comprises the detection of a bacterial infection in the subject. In still further embodiments, the determining of a concurrent infection comprises the detection of a viral infection in the subject.

In still further embodiments, the present invention provides a kit, comprising reagents for the detection of the amount of a CXCR3 ligand or CCR-5 receptor ligand (e.g., CCL chemokines) in a urine sample from a subject suspected of having acute renal failure, renal tubular interstitial disease or glomerulonephritis, and instructions for using the reagents for detecting the presence of the ligand in the urine sample. The present invention is not limited to the detection of a particular ligand. Any suitable ligand is contemplated including, but not limited to, IP-10, Mig, I-TAC, MIP-1α, MIP-3α, and MIP-1β. The present invention is not limited to a particular assay. In some embodiments, the reagents comprise reagents for performing an immunoassay. For example, any suitable immunoassay is contemplated including, but not limited to, ELISA, radio-immunoassay, automated immunoassay, cytometric bead assay, and immunoprecipitation assay. In some embodiments, the ELISA is a quantitative ELISA assay. In other embodiments the assay is a Luminex bead assay. In further embodiments, the assay is a protein microarray. In some embodiments, the instructions comprise instructions required by the United States Food and Drug Administration for use in in vitro diagnostic products. In some embodiments, the kit further comprises second reagents for determining the presence or absence of a concurrent infection in the subject and second instructions for using the reagent for determining the presence of absence of the concurrent infection in the subject. In some embodiments, the second instructions comprise instructions for determining the body temperature of the subject. In other embodiments, the second reagents comprise reagents for the detection of a bacterial infection in the subject. In still further embodiments, the second reagents comprise reagents for the detection of a viral infection in the subject. In some embodiments, the instructions further comprise instructions for using the kit for diagnosing tubular interstitial disease. In other embodiments, the instructions further comprise instructions for using the kit for predicting the risk of renal tubular injury.

DESCRIPTION OF THE FIGURES

FIG. 3 shows a comparison of kidney graft recipients with acute rejection, borderline rejection, BK virus nephritis, acute tubular injury, chronic rejection stable graft function and healthy controls with urinary chemokine levels greater than 100 pg/mL.

FIG. 4 shows values of IP-10/Mig in differentiation of recipients with acute dysfunction (for example, acute rejection, acute tubular injury and BK virus nephritis) from recipients with chronic rejection and stable graft function.

FIG. 8 shows the urine levels (mean,±standard error) of 23 cytokines, cytokine-related compounds, and chemokines classified into 3 groups (I, II, III) from patient samples (acute renal rejection, acute tubular necrosis, chronic allograft nephropathy, stable functioning renal grafts), and from healthy control individuals. Group I factors, which include angiogenin, TIMP-2, TNF sR2 and Trail R3 show a relatively high level in the urine samples from all participants. Group II factors, which include IL-1β, IL-2sRα, IL-6, MIP-1α, MIP-1β, MIP-3α, IL-18, and TNF-α show a relatively low level in the urine samples obtained from all participants. To the contrary, in comparison the results observed with factors from Groups I and II, Group III factors, which include adiponectin, IGFBP-1, IGFBP-2, IGFBP-6, IL-8, leptin, MCP-1, MIP-1δ, TNF sR1, osteoprotogerin (OPG), and uPAR, show low levels of factors in the urine samples of healthy participants, but specific patterns of elevation for each of the categories of kidney disorder. For example: adiponectin is elevated in all conditions tested; IGFBP-1, IGFBP-2 and IGFBP-6 are elevated in all conditions, but particularly so in acute tubular necrosis and chronic allograft nephropathy; IL-8 is elevated in acute tubular necrosis and stable grafts; leptin is elevated in acute tubular necrosis, but particularly so in acute rejection; MCP-1 is elevated in acute rejection, acute tubular necrosis and to a lesser extent in chronic allograft nephropathy; MIP-1δ is elevated in stable grafts, but is markedly elevated in acute rejection, acute tubular necrosis and chronic allograft nephropathy; TNF sR1 is elevated in all kidney disorders tested; and osteoprotogerin (OPG) and uPAR are elevated in all conditions but particularly so in acute rejection, acute tubular necrosis, and chronic allograft nephropathy.

FIG. 9 also shows that MIP-1δ and OPG are significantly elevated in samples from recipients with AR and ATN, but unlike IP-10 and Mig, MIP-1δ and OPG are also significantly elevated in samples from patients with borderline rejection, ABAR and CAN, but not in patients with BKVN. Similar to the results observed for IP-10 and Mig, MIP-1δ and OPG are not elevated in samples collected from recipients with stable graft function or from healthy individuals.

FIG. 10 also shows that urine levels of MIP-1δ and OPG differentiate AR, ABAR, ATN, BKVN, borderline rejection and CAN from stable graft function with high sensitivity and specificity as depicted in ROC curves.

FIG. 11 shows that with 80 pg/ml of IP-10, Mig, MIP-1δ and OPG in urine established as a cutoff level (that is, to provide maximal sensitivity and specificity), the majority of renal graft recipients with AR, ABAR, ATN or BKVN have high levels of IP-10 and Mig, while the majority of renal graft recipients with CAN or stable graft function have IP-10 and Mig levels below the cutoff.

FIG. 12 shows the sensitivity, specificity, positive predictive value and negative predictive value of IP-10, Mig to differentiate acute injury (AR, ABAR, ATN and BKVN) from CAN, stable graft function and healthy renal function. FIG. 12 also shows that MIP-1δ and OPG are both highly sensitive and specific to differentiate acute injury (AR, ABAR, ATN and BKVN), borderline rejection and CAN, from stable graft function and healthy renal function.

DEFINITIONS

Figure 1:
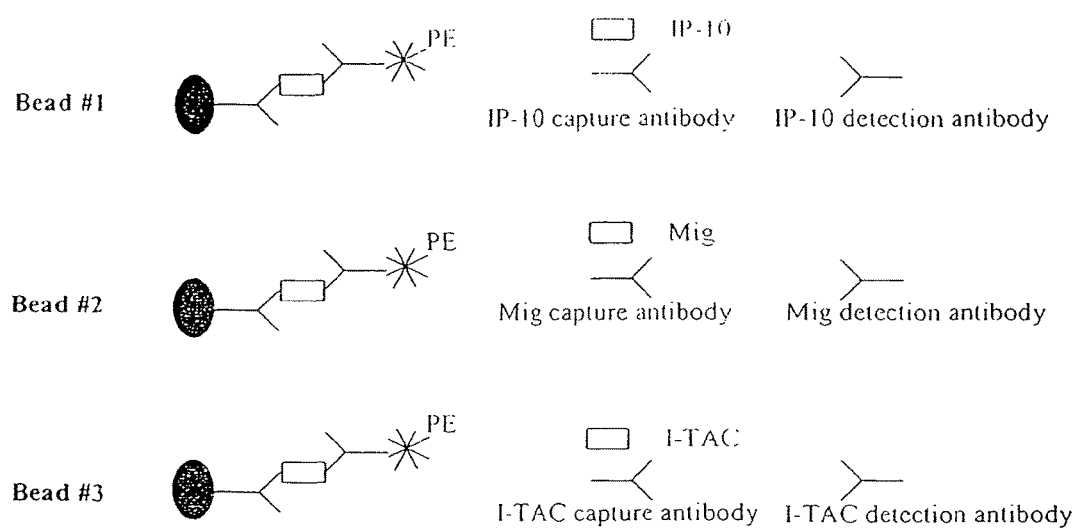
FIG. 1 shows the design of the Beads FACS method for quantification of chemokines IP-10, Mig, and I-TAC used in some embodiments of the present invention.

To facilitate an understanding of the present invention, a number of terms and phrases are defined below:

As used herein, the term "surgical procedure" refers to any procedure that involves treatment of injury, deformity, or disease by manual or instrumental means.

As used herein, the term "fluorescently activated cell sorting assay" (FACS) refers to any assay suitable for use in cell sorting techniques (e.g., flow cytometry) that employs detection of fluorescent signals.

As used herein, the terms "immunoglobulin" or "antibody" refer to proteins that bind a specific antigen. Immunoglobulins include, but are not limited to, polyclonal, monoclonal, chimeric, and humanized antibodies, Fab fragments, F(ab')$_2$ fragments, and includes immunoglobulins of the following classes: IgG, IgA, IgM, IgD, IbE, and secreted immunoglobulins (sIg). Immunoglobulins generally comprise two identical heavy chains and two light chains. However, the terms "antibody" and "immunoglobulin" also encompass single chain antibodies and two chain antibodies.

As used herein, the term "antigen binding protein" refers to proteins that bind to a specific antigen. "Antigen binding proteins" include, but are not limited to, immunoglobulins, including polyclonal, monoclonal, chimeric, and humanized antibodies; Fab fragments, F(ab')$_2$ fragments, and Fab expression libraries; and single chain antibodies.

The term "epitope" as used herein refers to that portion of an antigen that makes contact with a particular immunoglobulin.

When a protein or fragment of a protein is used to immunize a host animal, numerous regions of the protein may induce the production of antibodies which bind specifically to a given region or three-dimensional structure on the protein; these regions or structures are referred to as "antigenic determinants". An antigenic determinant may compete with the intact antigen (i.e., the "immunogen" used to elicit the immune response) for binding to an antibody.

The terms "specific binding" or "specifically binding" when used in reference to the interaction of an antibody and a protein or peptide means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A," the presence of a protein containing epitope A (or free, unlabelled A) in a reaction containing labeled "A" and the antibody will reduce the amount of labeled A bound to the antibody.

As used herein, the terms "non-specific binding" and "background binding" when used in reference to the interaction of an antibody and a protein or peptide refer to an interaction that is not dependent on the presence of a particular structure (i.e., the antibody is binding to proteins in general rather that a particular structure such as an epitope).

As used herein, the term "subject" refers to any animal (e.g., a mammal), including, but not limited to, humans, non-human primates, rodents, and the like, which is to be the recipient of a particular diagnostic test or treatment. Typically, the terms "subject" and "patient" are used interchangeably herein in reference to a human subject. As used herein, "cytokine" refers to any of a class of immunoregulatory substances (for example, lymphokines) that are secreted by cells of the immune system. As used herein, "cytokine-related compound" refers to any of a class of substances that are functionally linked to one or more cytokines, for example, adhesion molecules, selectins, integrins, chemokines, and chemokine receptors.

As used herein. "chemokines" are cytokines characterized, for example, by their ability to induce directed migration of leukocytes, leukocyte activation and effector function. As used herein, "chemokines" can be divided into, for example, four branches (C, CC, CXC, and CX3C) based upon the position of the first two cysteine residues in a four-cysteine motif in their primary amino acid sequence. As used herein, chemokines are also classified by their binding characteristics as ligands (L), for example CL, CCL, CXCL and CX3CL. As used herein, "chemokines" are further characterized based on whether they are inflammatory or homeostatic.

As used herein, in some embodiments "chemokines" are CXCR3 chemokines, including, but not limited to, IP-10, Mig, and I-TAC. In other embodiments, "chemokines" are CCL class chemokines, which bind to the CCR-5 receptor. Exemplary CCL class chemokines include, but are not limited to, MIP-1α, MIP-3α, and MIP-1β.

As used herein, the term "acute renal failure" refers to an abrupt and sustained decrease in glomerular filtration, urine output, or both. For example, acute renal failure may be an abrupt (1-7 days) and sustained (greater than 24 hours) change from baseline glomerular filtration rate, urine output, or both.

As used herein, "kidney disorder" refers to any pathologic disease or condition of the kidney including, for example, those diseases and conditions considered in Comprehensive Clinical Nephrology, 2nd Edition, edited by Richard J Johnson and John Feehally, Mosby, 2003, which is incorporated herein by reference in its entirety.

As used herein, "diagnosing disorders of the kidney" refers to, for example, the detection, identification, monitoring, and screening of kidney disorders. In some embodiments the diagnosis uses only the assays of the present invention. In other embodiments, assays of the present invention are used for diagnosis of a kidney disorder in combination with other indices of kidney function including, for example, patient signs and symptoms, tests of general kidney function, for example, serum creatinine and blood urea nitrogen (BUN), or urinalysis, or tests of specific disorders of the kidney, for example, kidney biopsy, urine RNA levels, urine DNA levels, and other urinary markers. In some embodiments, assays of the present invention are used, for example, for differential diagnosis between two or more possible diseases or conditions, or for the detection of two or more diagnoses of kidney disorders in the same patient. In some embodiments, assays of the present invention are performed in a health care facility laboratory. In other embodiments, assays of the present invention are performed in a reference clinical laboratory. In further embodiments, assays of the present invention are performed at the patient's residence by the patient, a caregiver, or health care provider.

In some embodiments or the present invention, diagnosing disorders of the kidney is based on detecting at least one compound from the list comprising adiponectin, IGFBP-1, IGFBP-2, IGFBP-6, IL-8, leptin, MCP-1, MIP-1δ, TNF sR1, osteoprotogerin, uPAR, IP-10 and Mig. As used herein, "detecting the presence" and "detecting the amount" of said compounds refer to a quantitative or qualitative measures of the compound in the urine of a subject. As used herein, "reagents for detection of at least one compound" and "reagents for detection of two or more compounds" refer to reagents specific for detection of the cytokines, cytokine-related compounds and chemokines of the present invention. In some embodiments, the reagent is an antibody. In other embodiments, the reagent is aptamer. In other embodiments, the reagents and kits of the present invention further comprise additional reagents and devices for performing detection assays, including, but not limited to, controls, buffers, and substrates (for example, beads, microspheres, and microarrays).

As used herein, the terms "instructions for using said reagents for detecting the presence of one or more said compounds", and "instructions for using said detecting the presence of one or more said compounds in said urine sample for diagnosing a kidney disorder" include instructions for using the reagents contained in the kit for the diagnosis of a kidney disorder in a sample from a subject. In some embodiments, the instructions further comprise the statement of intended use required by the U.S. Food and Drug Administration (FDA) in labeling in vitro diagnostic products. Information required in an application may include: 1) The in vitro diagnostic product name, including the trade or proprietary name, the common or usual name, and the classification name of the device; 2) The intended use of the product; 3) The establishment registration number, if applicable, of the owner or operator submitting the submission; the class in which the in vitro diagnostic product was placed under section 513 of the FD&C Act, if known, its appropriate panel, or, if the owner or operator determines that the device has not been classified under such section, a statement of that determination and the basis for the determination that the in vitro diagnostic product is not so classified; 4) Proposed labels, labeling and advertisements sufficient to describe the in vitro diagnostic product, its intended use, and directions for use, including photographs or engineering drawings, where applicable; 5) A statement indicating that the device is similar to and/or different from other in vitro diagnostic products of comparable type in commercial distribution in the U.S., accompanied by data to support the statement; 6) A summary of the safety and effectiveness data upon which the substantial equivalence determination is based; or a statement that the safety and effectiveness information supporting the FDA finding of substantial equivalence will be made available to any person within 30 days of a written request; 7) A statement that the submitter believes, to the best of their knowledge, that all data and information submitted in the premarket notification are truthful and accurate and that no material fact has been omitted; and 8) Any additional information regarding the in vitro diagnostic product requested that is necessary for the FDA to make a substantial equivalency determination. Additional information is available at the Internet web page of the U.S. FDA.

As used herein, the term "determining a treatment course of action" as in "determining a treatment course of action based on said diagnosis of a kidney disorder" refers to the choice of treatment administered to a patient. For example, if a patient is found to be at increased risk of a kidney disorder, therapy may be started, increased, or changed from one treatment type (e.g., pharmaceutical agent, surgery) to another. Conversely, if a patient is found to be at low risk for a kidney disorder, therapy may not be administered or levels of therapy may be decreased. In some embodiments, the treatment course of action is "continued monitoring" in which no treatment is administered but the levels of cytokines, cytokine-related compounds and chemokines measured in the patients urine is monitored regularly (e.g., using the diagnostic methods of the present invention). In other embodiments, the "treatment course of action" as used herein, comprises use of the results of the cytokine, cytokine-related compound and chemokine assays of the present invention as indicators of the need for additional tests of a kidney disorder, for example, an imaging scan, biopsy or ureteroscopic exam.

As used herein, the term "determining the efficacy of said acute renal failure, renal tubular interstitial disease or glomerulonephritis drug based on said detecting" refers to determining if a drug is preventing acute renal failure, renal tubular interstitial disease or glomerulonephritis based on, for example, detecting the level of cytokines, cytokine-related compounds and chemokines in the urine of a patient who manifests signs and symptoms of, or is at risk for acute renal failure, renal tubular injury or glomerulonephritis.

As used herein, the terms "computer memory" and "computer memory device" refer to any storage media readable by a computer processor. Examples of computer memory include, but are not limited to, RAM, ROM, computer chips, digital video disc (DVDs), compact discs (CDs), hard disk drives (HDD), and magnetic tape.

As used herein, the term "computer readable medium" refers to any device or system for storing and providing information (e.g., data and instructions) to a computer processor. Examples of computer readable media include, but are not limited to, DVDs, CDs, hard disk drives, magnetic tape and servers for streaming media over networks.

As used herein, the terms "processor" and "central processing unit" or "CPU" are used interchangeably and refer to a device that is able to read a program from a computer memory (e.g., ROM or other computer memory) and perform a set of steps according to the program.

As used herein, the term "non-human animals" refers to all non-human animals including, but not limited to, vertebrates such as rodents, non-human primates, ovines, bovines, ruminants, lagomorphs, porcines, caprines, equines, canines, felines, ayes, etc.

"Amino acid sequence" and terms such as "polypeptide" or "protein" are not meant to limit the amino acid sequence to the complete, native amino acid sequence associated with the recited protein molecule.

The term "native protein" as used herein to indicate that a protein does not contain amino acid residues encoded by vector sequences; that is, the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four amino acid residues to the entire amino acid sequence (that is, the "full size" sequence) minus one amino acid.

The term "Western blot" refers to the analysis of protein(s) (or polypeptides) immobilized onto a support such as nitrocellulose or a membrane. The proteins are run on acrylamide gels to separate the proteins, followed by transfer of the protein from the gel to a solid support, such as nitrocellulose or a nylon membrane. The immobilized proteins are then exposed to antibodies with reactivity against an antigen of interest. The binding of the antibodies may be detected by various methods, including the use of radiolabeled antibodies.

As used herein, the terms "protein microarray" and "protein chip" refer to protein-detecting molecules immobilized at high density on a substrate, and probed for various biochemical activities. (See, for example: Zhu H and Snyder M, "Protein chip technology", Current Opinion in Chemical Biology 7: 55-63, 2003; Cutler P, "Protein arrays: The current state of the art", Proteomics 3; 3-18, 2003; and MacBeath G, "Protein microarrays and proteomics", Nature Genetics Supplement 32: 526-532, 2002, each of which is incorporated herein by reference in its entirety).

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

The terms "test compound" and "candidate compound" refer to any chemical entity, pharmaceutical, drug, and the like that is a candidate for use to treat or prevent a disease, illness, sickness, or disorder of bodily function (for example, renal acute renal failure, renal tubular interstitial disease, renal cancer or glomerulonephritis). Test compounds comprise both known and potential therapeutic compounds. A test compound can be determined to be therapeutic by screening using the screening methods of the present invention.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include urine and blood products, such as plasma, serum and the like. Such examples are not however to be construed as limiting the sample types applicable to the present invention.

DETAILED DESCRIPTION OF THE INVENTION

The present invention relates to methods of diagnosing, predicting and monitoring kidney disorders. In particular, the present invention relates to the diagnosis, prediction and monitoring of kidney disorders by detection of cytokines, cytokine-related compounds and chemokines in urine. The present invention further relates to methods and compositions for assessing the efficacy of agents and interventions used to treat kidney disorders.

For example, the present invention provides a novel, non-invasive method of correlating the presence of certain cytokines, cytokine-related compounds and chemokines s in urine with acute renal failure, renal tubular interstitial disease, renal cancer or glomerulonephritis. The methods are a significant improvement over invasive biopsy in terms of decreased cost and physical trauma to a patient. The methods of the present invention provide the further advantage of allowing home testing by patients.

I. Detection of Cytokines, Cytokine-related Compounds and Chemokines in Urine

In some embodiments, the present invention provides methods of predicting and diagnosing a kidney disorder by detecting cytokines, cytokine-related compounds and chemokines in urine. The present invention is not limited to a particular detection assay. The description below provides non-limiting examples of suitable cytokines, cytokine-related compounds and chemokines and detection methods. The present invention further provides kits for use in detecting cytokines, cytokine-related compounds and chemokines in urine.

A. Urinary Cytokines, Cytokine-related Compounds and Chemokines

The present invention provides methods of detecting cytokines, cytokine-related compounds and chemokines in urine. The urinary cytokines, cytokine-related compounds and chemokines of the present invention are correlated with the presence or absence of kidney disorders, for example acute renal failure, renal tubular interstitial disease, renal cancer or glomerulonephritis. In some embodiments, the presence of the peptides or an increased amount of the peptides is indicative of tubular injury. In other embodiments, increased urinary cytokines, cytokine-related compounds and chemokines are correlated with increased risk of acute renal failure, renal interstitial disease, renal cancer or glomerulonephritis. In preferred embodiments, the amount of urinary cytokine, cytokine-related compound and chemokine is quantitated. In some preferred embodiments, a quantitative level of urinary cytokine, cytokine-related compound and chemokine is determined that is indicative of an increased risk of a kidney disorder. In other embodiments, the level of cytokine, cytokine-related compound and chemokine is correlated with a functioning level of a drug (e.g., the correct amount or a functional drug).

In preferred embodiments, the chemokines are CXCR3 chemokines. CXCR3 chemokines include, but are not limited to, IP-10, Mig, and I-TAC. In other embodiments, the chemokines are CCL chemokines. CCL chemokines bind to the CCR-5 receptor and include, but are not limited to, MIP-1α, MIP-3α, and MIP-1β. In particularly preferred embodiments, the cytokines, cytokine-related compounds and chemokines are selected from the list comprising adiponectin, IGFBP-1, IGFBP-2, IGFBP-6, IL-8, leptin, MCP-1, MIP-1δ, TNF sR1, osteoprotogerin, uPAR, IP-10 and Mig.

In some embodiments, two or more (e.g., 3 or more, 4 or more, etc.) cytokines, cytokine-related compounds and chemokines are detected to provide a risk assessment. The presence of each marker may provide a more definitive answer than the analysis of any single marker alone. For example, as described in Example 2 below, detection of both IP-10 and I-TAC provided a 100% correlation to renal failure in the patient group tested.

In some embodiments, certain threshold levels of a particular marker are detected. If the threshold level is reached, risk of acute renal failure, tubular interstitial disease, renal cancer or glomerulonephritis is observed. For example, if 100 pg/ml of the rejection marker (e.g., IP-10, I-TAC) in urine is observed, risk is observed. Or, for example, if 80 pg/ml of the marker for a kidney dysfunction is reached (for example, adiponectin, IGFBP-1, IGFBP-2, IGFBP-6, IL-8, leptin, MCP-1, MIP-1δ, TNF sR1, osteoprotogerin, uPAR, IP-10 and Mig), increase risk for a kidney disorder is observed. The present invention is not limited by the threshold level used in the analysis. In some embodiments, the threshold level is 20 pg/ml or more, more preferably, 50 pg/ml or more, preferably 80 pg/ml, and most preferably 100 pg/ml or more, although both higher and lower threshold values are contemplated, as are intervals between these values.

B. Detection Methods

The present invention provides methods for detecting the presence of cytokines, cytokine-related compounds and chemokines in a urine sample. In some embodiments, a full-size cytokine, cytokine-related compound or chemokine polypeptide is detected. In other embodiments, a fragment or a portion of a cytokine, cytokine-related compound or chemokine polypeptide is detected. In preferred embodiments, the present invention additionally provides methods of quantifying the amount of a cytokine, cytokine-related compound and chemokine in urine. The present invention is not limited to a particular detection assay. In some embodiments detection is, for example, fluorescent detection, spectrometric detection, chemiluminescent detection, matrix assisted laser desorption-time-of flight (MALDI-TOF) detection, high pressure liquid chromatographic detection, charge detection, mass detection, radio frequency detection, and light diffraction detection. Exemplary detection assays are described herein.

In some embodiments, cytokines, cytokine-related compounds and chemokines are detected by binding of a capture molecule specific for the protein (for example, an aptamer, or an antibody in an immunoassay). The present invention is not limited to a particular capture molecule or antibody. Any capture molecule or antibody (e.g., monoclonal or polyclonal) that detects cytokines, cytokine-related compounds and chemokines may be utilized. Exemplary methods for the generation of antibodies are described below.

Antibody binding is detected by techniques known in the art. For example, in some embodiments, antibody binding is detected using a suitable technique, including but not limited to, radio-immunoassay, ELISA (enzyme-linked immunosorbant assay), "sandwich" immunoassay, immunoradiometric assay, gel diffusion precipitation reaction, immunodiffusion assay, precipitation reaction, agglutination assay (e.g., gel agglutination assay, hemagglutination assay, etc.), complement fixation assay, immunofluorescence assay, protein A assay, and immunoelectrophoresis assay.

In some preferred embodiments, a quantitative ELISA assay is utilized (See e.g., U.S. Pat. Nos. 5,958,715, and 5,484,707, each of which is herein incorporated by reference). In some preferred embodiments, the quantitative ELISA is a competitive ELISA. In a competitive ELISA, the wells of a microtiter plate are first coated with a fusion protein comprising all or a fragment of the cytokine, cytokine-related compound or chemokine (e.g., a CXCR3 or CCL ligand). The sample to be tested is added to the plate along with an antibody that is specific for the cytokine, cytokine-related compound or chemokine. The cytokine, cytokine-related compound or chemokine in the urine sample competes for binding to the antibody with the immobilized peptide. The plate is washed and the antibody bound to the immobilized cytokine, cytokine-related compound or chemokine polypeptide is then detected using any suitable method (e.g., a secondary antibody comprising a label or a group reactive with an enzymatic detection system). The amount of signal is inversely proportional to the amount of cytokine, cytokine-related compound or chemokine polypeptide present in the urine sample (e.g., a high signal is indicative of low amounts of cytokine, cytokine-related compound or chemokine polypeptide being present in the urine).

In some embodiments, an automated detection assay is utilized. Methods for the automation of immunoassays include, but are not limited to, those described in U.S. Pat. Nos. 5,885,530, 4,981,785, 6,159,750, and 5,358,691, each of which is herein incorporated by reference. In some embodiments, the analysis and presentation of results is also automated. For example, in some embodiments, software that generates a diagnosis and/or prognosis based on the level of cytokine, cytokine-related compound or chemokine polypeptide in the urine is utilized. In other embodiments, the immunoassay described in U.S. Pat. Nos. 5,789,261, 5,599,677 and 5,672,480, each of which is herein incorporated by reference, is utilized.

In still other embodiments, a protein microarray or protein chip array assay is utilized for detection (See e.g., U.S. Pat. No. 6,197,599, herein incorporated by reference). In such an assay, proteins (e.g., antibodies specific for a cytokine, cytokine-related compound or chemokine polypeptide) are immobilized on a solid support such as a chip. A urine sample suspected of containing the cytokine, cytokine-related compound or chemokine polypeptide is passed over the solid support. Bound cytokine, cytokine-related compound or chemokine polypeptides are then detected using any suitable method. In some embodiments, detection is via surface plasmon resonance (SPR) (See e.g., WO 90/05305, herein incorporated by reference). In SPR, a beam of light from a laser source is directed through a prism onto a biosensor consisting of a transparent substrate, usually glass, which has one external surface covered with a thin film of a noble metal, which in turn is covered with an organic film that interacts strongly with an analyte, such as a biological, biochemical or chemical substance. The organic film contains antibodies (e.g., specific for a cytokine, cytokine-related compound or chemokine polypeptide of the present invention), which can bind with an analyte (e.g., chemokine) in a sample to cause an increased thickness, which shifts the SPR angle. By either monitoring the position of the SPR angle, or the reflectivity at a fixed angle near the SPR angle, the presence or absence of an analyte in the sample can be detected.

In other embodiments, The PROTEINCHIP (Ciphergen Biosystems, Fremont, Calif.) is utilized for detection. The PROTEINCHIP system uses SELDI (Surface-Enhanced Laser Desorption/Ionization) technology to perform the separation, detection and analysis of proteins at the femtomole level directly from biological samples (See e.g., U.S. Pat. No. 6,294,790 and U.S. Patent Application US20010014461A1, each of which is herein incorporated by reference. In the PROTEINCHIP technology, proteins of interest (e.g., cytokine, cytokine-related compound or chemokine polypeptides) are captured on the PROTEINCHIP Array (e.g., via a bound antibody) directly from the original source material. The chip is washed to remove undesired materials and bound proteins are detected using SELDI.

In some embodiments, a cytometric bead array assay is used (Quantum Plex kit, Bangs Laboratories; Cytometric Bead Array kit, BD Biosciences). These systems allow for multiple analyte detection with small volume samples. In other embodiments, a Luminex bead assay is used.

The present invention is not limited to the detection of cytokines, cytokine-related compounds and chemokines in urine. Any bodily fluid that contains elevated levels of cytokine, cytokine-related compound and chemokine correlated with a kidney disorder may be utilized, including, but not limited to, blood, serum, lymph, and saliva.

In some particularly preferred embodiments, a combination of several cytokines, cytokine-related compounds or chemokines are detected simultaneously in urine samples. In some embodiments, the present invention provides a fluorescently activated cell sorting (FACS) method for the simultaneous detection of multiple cytokines, cytokine-related compounds or chemokines. In some embodiments, the method uses fluorescence dye labeled beads that can detect multiple (e.g., at least 3) cytokines, cytokine-related compounds or chemokines in one assay. In one exemplary embodiment (Example 3), the assay was used to detect IP-10, I-TAC and Mig. Detection of these three chemokines was conducted in the same test tube simultaneously as depicted in FIG. 1. As the chemokine concentration increases, the mean fluorescence intensity for each group of beads increases. This correlation between the chemokine concentration and the mean fluorescence establishes the basis for this FACS quantitative method. A standard curve for each chemokine was constructed. These results demonstrate a quantitative assay for the simultaneous detection of multiple cytokines, cytokine-related compounds and chemokines.

The present invention is further not limited to the direct detection of cytokine, cytokine-related compound and chemokine polypeptides. The present invention contemplates the detection of correlated polypeptides or compounds (e.g., cytokine, cytokine-related compound and chemokine DNA, mRNA, metabolites, etc.). In still further embodiments, the present invention provides methods of detecting the interaction of cytokines, cytokine-related compounds and chemokines with cytokine, cytokine-related compound and chemokine receptors (e.g., CXCR3 or CCR-5 receptors).

C. Detection of Concurrent Infection

In some embodiments, assays for the detection of cytokines, cytokine-related compounds and chemokines are combined with assays for the detection of concurrent infections (e.g., bacterial or viral infections) that may generate false-positive results. For example, infection may cause elevated levels of cytokines, cytokine-related compounds and chemokines. In some embodiments, the presence of infection is monitored along with the presence of cytokines, cytokine-related compounds and chemokines.

In some embodiments, infection is monitored by the presence of diagnostic symptoms (e.g., including, but not limited to, elevated body temperature, swelling or redness, and pain). In other embodiments, infection is monitored by monitoring the presence of infectious organisms such a bacteria, virus, or fungus. In still further embodiments, infection is monitored by monitoring the presence of elevated cytokines, cytokine-related compounds and chemokines that are associated with infection, but not with a general or specific kidney disorder. In yet other embodiments, infection is monitored by an elevated white blood cell count in a subject.

D. Kits

In some embodiments, the present invention provides kits for the detection of cytokines, cytokine-related compounds and chemokines. In some embodiments, the kits contain antibodies specific for cytokines, cytokine-related compounds and chemokines in addition to detection reagents, buffers or devices. In some embodiments, the kits contain reagents and/or instructions for testing for concurrent infections. In preferred embodiments, the kits contain all of the components necessary to perform a detection assay, including all controls, directions for performing assays, and any necessary hardware or software for analysis and presentation of results.

In some embodiments, the kits contain an assay in a test strip format. In such embodiments, the detection reagent (e.g., antibody), as well as any control or secondary antibodies, are affixed to a solid support. In some embodiments, the solid support is a test strip suitable for dipping into a solution of urine (See e.g., U.S. Pat. Nos. 6,352,862, 6,319, 676, 6,277,650, 6,258,548, and 6,248,596, each of which is herein incorporated by reference).

In some embodiments, the kits are marketed as in vitro diagnostics. The marketing of such kits in the United States requires approval by the Food and Drug Administration (FDA). The FDA classifies in vitro diagnostic kits as medical devices. The 510(k) regulations specify categories for which information should be included.

II. Patient Care

The present invention further provides methods of providing test kits to patients in a variety of settings. The test kits of the present invention are suitable for use in both clinical and home testing settings. In preferred embodiments, test kits are approved for sale as in vitro diagnostics as described above.

A. Home Testing

In some embodiments, the present invention provides kits for home testing. In preferred embodiments, the kits are approved as in vitro diagnostics for home use under guidelines as described above. Patients may use home test kits to monitor acute renal failure, renal tubular interstitial disease, renal cancer or glomerulonephritis. In some embodiments, test kits for home use are qualitative rather than quantitative. For example, in some embodiments, the test registers a positive result if urine levels of cytokines, cytokine-related compounds and chemokines are above a pre-determined level (e.g., above approximately 80 pg/mL) or increase over time. In other embodiments, the tests are quantitative (e.g., utilizing the quantitative methods described above).

For example, in some embodiments, patients at risk for a kidney disorder monitor urine levels of cytokines, cytokine-related compounds and chemokines. In preferred embodiments, patients conduct serial monitoring (e.g., from once a day to once a month or every several months) to screen for early signs or renal failure. In preferred embodiments, patients whose urine levels of cytokines, cytokine-related compounds and chemokines are above a pre-determined level (or register a positive result in a quantitative assay) are instructed to seek medical advice.

In other embodiments, the test kits are utilized by patients, caregivers or health care providers at the patient's residence to monitor the effectiveness of a drug. For example, in some embodiments, a patient who is taking a drug following the diagnosis of a kidney disorder monitors levels of cytokines, cytokine-related compounds and chemokines on a regular basis (e.g., from once a day to once a month or every several months). If a patient's levels of cytokines, cytokine-related compounds or chemokines are above a pre-determined level (or registers a positive result in a quantitative assay), it may be indicative of organ failure caused by lack of an effective level of a drug. Such patients are advised to schedule a follow up with a caregiver (e.g., to adjust the medication levels, or switch to a different drug).

B. Clinical-Based Testing

In other embodiments, testing is performed in a clinical (e.g., hospital or clinic) setting. In such embodiments, testing is generally ordered and interpreted by a physician or other clinician. In some embodiments, testing is carried out by a lab technician (e.g., in an in-house or external clinical lab). In preferred embodiments, clinical testing utilizes a quantitative assay for detection of cytokines, cytokine-related compounds and chemokines. In some embodiments, testing is utilized to determine the likelihood of organ failure in a patient with a kidney disorder. In other embodiments, testing is utilized to monitor organ function in a subject who has recovered from a kidney disorder, and is not on medication. In still further embodiments, testing is utilized to monitor the effectiveness of a medication. In some embodiments, the urinary cytokine, cytokine-related compound or chemokine test is used to complement allograft biopsy and serum creatinine (Cr), and to monitor response to therapy. In a preferred embodiment, the urinary cytokine, cytokine-related compound and chemokine test is used as a reference parameter in deciding whether and when a biopsy should be taken. Combining serum Cr with the urinary cytokines, cytokine-related compounds and chemokines test distinguishes acute dysfunction of the renal allograft, which is medical emergency and needs urgent treatment, from non-acute elevations of serum creatinine (Cr) and dysfunction. For patients with elevated Cr and, for example, urinary IP-10/Mig, a biopsy should be immediately taken and an accurate diagnosis should be made before the initiation of therapy. In another embodiment, in patients who have concurrent elevation of serum Cr and urinary cytokines, cytokine-related compounds or chemokines, if a BK virus test on urinary cells either by microscopic observation or polymerase chain reaction is also positive, the likelihood of BK virus nephritis is very high, and a biopsy may be avoided. In a further embodiment, if the serum Cr is increased, but there is a normal level of urinary cytokines, cytokine-related compounds and chemokines, elevation of serum Cr may be due to chronic insidious damage to the renal graft. In this circumstance, a biopsy is delayed or even avoided. In still further embodiments, urine cytokine, cytokine-related compound and chemokine levels are useful in patients whose biopsy reveals borderline rejection in assessing the need for anti-rejection therapy. In yet further embodiments, the urine cytokine, cytokine-related compound and chemokine test distinguishes active low-grade damage in patients having dormant infiltrating immune cells as found in many biopsies from renal grafts reveal numerous infiltrating immune cells. These patients often have a normal serum Cr. In additional embodiments, the urinary cytokine, cytokine-related compound and chemokine test is used as an early index of the response to anti-rejection therapy. In particularly preferred embodiments, the urinary IP-10 test is useful in recipients with acute rejection that is superimposed on chronic injury causing an elevated baseline of serum Cr. In these patients serum Cr may not return to the baseline level, but the urinary IP-10 will decline as acute injury resolves.

The urinary cytokine, cytokine-related compound and chemokine test of the present invention is simple to conduct and rapid, making it suitable for clinical use. In some embodiments, testing is utilized as a follow up to home testing by a patient (e.g., when cytokines, cytokine-related compound and chemokines levels are elevated or the patient has other clinical signs or symptoms of a kidney disorder). Based on the result of the clinical testing, the appropriate intervention is taken (e.g., including, but not limited to, an increase or decrease in levels of drug therapy, initiation of drug therapy, termination of therapy, surgery, further testing, or continued monitoring).

C. Home Collection/Clinic Testing

In still further embodiments, testing is provided by a clinical lab but in the absence of a physician's order or interpretation. For example, in some embodiments, the patient collects a urine specimen and transports the specimen to a clinical lab (e.g., by mail or in person). The clinical lab then reports the result to the patient. In other embodiments, the patient provides a sample at a clinical lab, the sample is analyzed, and the results are returned to the patient. The patient then decides, based on the level of cytokines, cytokine-related compounds and chemokines in the urine (or the presence or absence of a positive result in a qualitative assay) whether or not to contact a physician for follow up care.

III. Antibodies

The present invention provides isolated antibodies. In preferred embodiments, the present invention provides monoclonal antibodies that specifically bind to an isolated polypeptide comprised of at least five amino acid residues of a cytokine, cytokine-related compound or chemokine. These antibodies find use in the diagnostic methods described herein. In other embodiments, commercially available antibodies are utilized (e.g., available from any suitable source including, but not limited to, R & D System, Minneapolis, Minn.).

An antibody against a protein of the present invention may be any monoclonal or polyclonal antibody, as long as it can recognize the protein. Antibodies can be produced by using a protein of the present invention as the antigen according to a conventional antibody or antiserum preparation process.

The present invention contemplates the use of both monoclonal and polyclonal antibodies. Any suitable method may be used to generate the antibodies used in the methods and compositions of the present invention, including but not limited to, those disclosed herein. For example, for preparation of a monoclonal antibody, protein, as such, or together with a suitable carrier or diluent is administered to an animal (e.g., a mammal) under conditions that permit the production of antibodies. For enhancing the antibody production capability, complete or incomplete Freund's adjuvant may be administered. Normally, the protein is administered once every 2 weeks to 6 weeks, in total, about 2 times to about 10 times. Animals suitable for use in such methods include, but are not limited to, primates, rabbits, dogs, guinea pigs, mice, rats, sheep, goats, etc.

For preparing monoclonal antibody-producing cells, an individual animal whose antibody titer has been confirmed (e.g., a mouse) is selected, and 2 days to 5 days after the final immunization, its spleen or lymph node is harvested and antibody-producing cells contained therein are fused with myeloma cells to prepare the desired monoclonal antibody producer hybridoma. Measurement of the antibody titer in antiserum can be carried out, for example, by reacting the labeled protein, as described hereinafter and antiserum and then measuring the activity of the labeling agent bound to the antibody. The cell fusion can be carried out according to known methods, for example, the method described by Koehler and Milstein (Nature 256:495 [1975]). As a fusion promoter, for example, polyethylene glycol (PEG) or Sendai virus (HVJ), preferably PEG is used.

Examples of myeloma cells include NS-1, P3U1, SP2/0, AP-1 and the like. The proportion of the number of antibody producer cells (spleen cells) and the number of myeloma cells to be used is preferably about 1:1 to about 20:1. PEG (preferably PEG 1000-PEG 6000) is preferably added in concentration of about 10% to about 80%. Cell fusion can be carried out efficiently by incubating a mixture of both cells at about 20° C. to about 40° C., preferably about 30° C. to about 37° C. for about 1 minute to 10 minutes.

Various methods may be used for screening for a hybridoma producing the antibody (e.g., against a CXCR3 or CCL ligand). For example, where a supernatant of the hybridoma is added to a solid phase (e.g., microplate) to which antibody is adsorbed directly or together with a carrier and then an anti-immunoglobulin antibody (if mouse cells are used in cell fusion, anti-mouse immunoglobulin antibody is used) or Protein A labeled with a radioactive substance or an enzyme is added to detect the monoclonal antibody against the protein bound to the solid phase. Alternately, a supernatant of the hybridoma is added to a solid phase to which an anti-immunoglobulin antibody or Protein A is adsorbed and then the protein labeled with a radioactive substance or an enzyme is added to detect the monoclonal antibody against the protein bound to the solid phase.

Selection of the monoclonal antibody can be carried out according to any known method or its modification. Normally, a medium for animal cells to which HAT (hypoxanthine, aminopterin, thymidine) are added is employed. Any selection and growth medium can be employed as long as the hybridoma can grow. For example, RPMI 1640 medium containing 1% to 20%, preferably 10% to 20% fetal bovine serum, GIT medium containing 1% to 10% fetal bovine serum, a serum free medium for cultivation of a hybridoma (SFM-101, Nissui Seiyaku) and the like can be used. Normally, the cultivation is carried out at 20° C. to 40° C., preferably 37° C. for about 5 days to 3 weeks, preferably 1 week to 2 weeks under about 5% $CO_2$ gas. The antibody titer of the supernatant of a hybridoma culture can be measured according to the same manner as described above with respect to the antibody titer of the anti-protein in the antiserum.

Separation and purification of a monoclonal antibody (e.g., against a CXCR3 or CCL ligand) can be carried out according to the same manner as those of conventional polyclonal antibodies such as separation and purification of immunoglobulins, for example, salting-out, alcoholic precipitation, isoelectric point precipitation, electrophoresis, adsorption and desorption with ion exchangers (e.g., DEAE), ultracentrifugation, gel filtration, or a specific purification method wherein only an antibody is collected with an active adsorbent such as an antigen-binding solid phase, Protein A or Protein G and dissociating the binding to obtain the antibody.

Polyclonal antibodies may be prepared by any known method or modifications of these methods including obtaining antibodies from patients. For example, a complex of an immunogen (an antigen against the protein) and a carrier protein is prepared, and an animal is immunized by the complex according to the same manner as that described with respect to the above monoclonal antibody preparation. A material containing the antibody against is recovered from the immunized animal and the antibody is separated and purified.

As to the complex of the immunogen and the carrier protein to be used for immunization of an animal, any carrier protein and any mixing proportion of the carrier and a hapten can be employed as long as an antibody against the hapten, which is crosslinked on the carrier and used for immunization, is produced efficiently. For example, bovine serum albumin, bovine cycloglobulin, keyhole limpet hemocyanin, etc. may be coupled to an hapten in a weight ratio of about 0.1 part to about 20 parts, preferably, about 1 part to about 5 parts per 1 part of the hapten.

In addition, various condensing agents can be used for coupling of a hapten and a carrier. For example, glutaraldehyde, carbodiimide, maleimide-activated ester, activated ester reagents containing thiol group or dithiopyridyl group, and the like find use with the present invention. The condensation product as such or together with a suitable carrier or diluent is administered to a site of an animal that permits the antibody production. For enhancing the antibody production capability, complete or incomplete Freund's adjuvant may be administered. Normally, the protein is administered once every 2 weeks to 6 weeks, in total, about 3 times to about 10 times.

The polyclonal antibody is recovered from blood, ascites and the like, of an animal immunized by the above method. The antibody titer in the antiserum can be measured according to the same manner as that described above with respect to the supernatant of the hybridoma culture. Separation and purification of the antibody can be carried out according to the same separation and purification method of immunoglobulin as that described with respect to the above monoclonal antibody.

The protein used herein as the immunogen is not limited to any particular type of immunogen. For example, a cytokine, cytokine-related compound or chemokine polypeptide (further including a gene having a nucleotide sequence partly altered) can be used as the immunogen. Further, fragments of the protein may be used. Fragments may be obtained by any methods including, but not limited to expressing a fragment of the gene, enzymatic processing of the protein, chemical synthesis, and the like.

IV. Drug Screening

In some embodiments, the present invention provides drug-screening assays (e.g., to screen for drugs effective in treating disorders of the kidney). The screening methods of the present invention utilize the detection of cytokines, cytokine-related compounds and chemokines. For example, in some embodiments, the present invention provides methods of screening for compounds that alter (e.g., increase or decrease) the expression of cytokines, cytokine-related compounds and chemokines. In some embodiments, the levels of cytokines, cytokine-related compounds and chemokines are detected (e.g., using a method described herein) in a subject that has undergone administration of a candidate compound. The increased levels of cytokines, cytokine-related compounds and chemokines are indicative of a candidate compound that is not preventing renal failure. Conversely, preferred candidate compounds are those that normalize cytokine, cytokine-related compound and chemokine levels.

In some embodiments, drug screening assays are performed in animals. Any suitable animal may be used including, but not limited to, baboons, rhesus or other monkeys, mice, or rats. Animal models of kidney disorders are generated (e.g., by the administration of compounds that trigger renal failure), and the effects of candidate drugs on the animals are measured. In preferred embodiments, kidney disorders in the animals are measured by detecting levels of cytokines, cytokine-related compounds and chemokines in the urine of the animals. The level of cytokines, cytokine-related compounds and chemokines may be detected using any suitable method, including, but not limited to, those disclosed herein.

EXPERIMENTAL

The following examples are provided in order to demonstrate and further illustrate certain preferred embodiments and aspects of the present invention, and are not to be construed as limiting the scope thereof.

Example 1

Correlation of Urine IP-10 with Graft Rejection

This example describes the correlation of urine levels of IP-10 with kidney graft rejection in human subjects. Forty-five human subjects that had undergone kidney transplant were investigated. Urine IP-10 levels were measured serially after organ transplantation. IP-10 levels were measured using a quantitative colorimetric sandwich ELISA assay (R & D Systems, Minneapolis, Minn.). Subjects were divided into two groups, rejecters and non-rejecters, based on kidney biopsies. Biopsies were classified using Banff criteria. All subjects were receiving anti-rejection therapy at the time of the study. Urine from ten normal (non-transplant) subjects was also tested.

In a majority of the non-rejecters, IP-10 levels remained at a constant, low level or decreased over time. In the rejecters, IP-10 levels remained at a constant, high level or increased over time. A urine level of IP-10 of greater than approximately 100 pg/mL was associated with organ rejection. There was no detectable IP-10 in any of the normal control samples. This Example demonstrates that IP-10 levels are correlated with kidney transplant rejection.

Experiments conducted during the development of the present invention also demonstrated a correlation between CCL chemokines and rejection. For example, correlations were observed for the CCL chemokines MIP-1α, MIP-3α, and MIP-1β

Example 2

Correlation of Urinary Chemokines with Graft Rejection and Treatment

This example describes the correlation of urinary chemokines levels with graft rejection and treatment. Urinary samples were collected from healthy individuals, kidney transplant recipients with stable graft function, and recipients with acute rejection. All patients with acute rejection were hospitalized and received anti-rejection therapy. Urinary samples were centrifuged, and supernatant was aliquoted and stored at −80° C. These samples, after thawing, were evaluated by ELISA for the expression of MCP-1, IP-10, and I-TAC.

Elevated Expression of Chemokines in Urinary Samples from Patients with Acute Rejection As shown in Table 1, chemokines IP-10 and I-TAC were significantly increased in the urinary samples of patients with acute graft rejection and acute tubular injury, compared to healthy controls and kidney transplant patients with other pathologic changes. As presented in Table 2, if 100 pg/ml was used as the cut-off level and IP-10 and I-TAC were considered simultaneously, 80% of samples from patients with rejection and acute tubular injury were above this level, but less than 5% of the patients in the remaining groups were above this level. This result indicates that detection of IP-10 and I-TAC in the urinary samples reflects the acute rejection/acute tubular injury in the kidney grafts.

MCP-1 was also examined in the urinary samples. In the present series of samples (Table 1), urinary MCP-1 was increased in patients with acute rejection or acute tubular injury. However, the difference of MCP-1 levels between acute rejection/acute tubular injury and the remaining groups of patients was not significant.

TABLE 1

Urinary Chemokine Levels in Patients with Kidney Transplant

| | Healthy Controls (n = 10) | Others (non-acute/Chronic Rejection; n = 16) | Chronic Rejection (n = 7) | Acute Tubular Injury (n = 3) | Suspicious Acute Rejection (n = 7) | Acute Rejection (n = 10) Day 1/Day 2* |
|---|---|---|---|---|---|---|
| IP-10 (pg/ml) | 1 | 12 | 31 | 362 | 27.8 | 376/579 |
| I-TAC (pg/ml) | 1 | 21 | 13 | 75 | 44 | 94.2/168 |
| MCP-1 (pg/ml) | 269 | 641 | 1908 | 3226 | 528 | 2060/2473 |

*Day 1/Day 2 indicates the biopsy day/the day after the biopsy day.

TABLE 2

Patients with Urinary IP-10 and I-TAC Levels above 100 pg/ml

| | Healthy Controls (n = 10) | Others (non-acute/Chronic Rejection; n = 16) | Chronic Rejection (n = 7) | Acute Tubular Injury (n = 3) | Suspicious Acute Rejection (n = 7) | Acute Rejection (n = 10) Day1/Day* |
|---|---|---|---|---|---|---|
| IP-10 | 0 | 0 | 0 | 3 | 1 | 7/6 |
| I-TAC | 0 | 0 | 0 | 1 | 0 | 4/6 |
| IP-10 or I-TAC | 0 | 0 | 0 | 3 | 1 | 8/8 |

*Day 1/Day 2 indicates the biopsy day/the day after the biopsy day.

Return of Urinary Chemokine Levels to Baseline after Resolution of Acute Rejection Urinary samples were collected daily from patients with biopsy-proven acute graft rejection until the rejection resolved. IP-10 and I-TAC were determined in these samples with ELISA. IP-10 and I-TAC were elevated at the time of diagnosis, but the levels decreased after anti-rejection therapy was started, and finally returned to the baseline. These results indicate that chemokine levels are useful parameters for monitoring the therapeutic response to anti-rejection therapies. In contrast, MCP-1 levels did not return to baseline in at least 50% of the patients with acute rejection following successful treatment. This example indicates that IP-10 and I-TAC levels correlate with acute rejection processes in the kidney graft.

Example 3

Flow Cytometry Based Technique for Quantification of Chemokines

This example describes a FACS method for the simultaneous detection of multiple chemokines. The fluorescence activated cell sorting (FACS) method uses fluorescence dye labeled beads that can detect 3 chemokines in one assay. In this example, IP-10, I-TAC and Mig were detected. Detection of the three chemokines was conducted in the same test tube simultaneously as depicted in FIG. 1. As the chemokine concentration increases, the mean fluorescence intensity for each group of beads increases. This correlation between the chemokine concentration and mean fluorescence establishes the basis for the FACS quantitative method. A standard curve for each chemokine was constructed. This example demonstrates that IP-10, Mig and I-TAC can be simultaneously detected in a urinary sample.

Example 4

Urinary Chemokine Assay Using the Luminex Microsphere Platform

Subjects

Ninety-nine renal allograft recipients were recruited and donated 350 urinary samples. Among the patients, 28 were diagnosed with acute rejection, 9 with borderline rejection, 6 with BK virus nephritis, 10 with acute tubular injury, 20 with chronic rejection, and 26 with stable graft function without graft injury. Urinary samples were also collected from 16 healthy non-transplanted individuals. Renal transplant recipients with symptoms and elevated serum creatinine (Cr) underwent renal transplant biopsy which was used as the diagnostic standard. Acute and chronic rejection events were scored according to Banff criteria by a renal transplant pathologist. BK virus infection was diagnosed using light microscopy identification of pleomorphic, enlarged tubular epithelial cell nuclei containing characteristic "smudgy" inclusions. The suspicion of BK virus infection was confirmed in all cases by immunohistochemistry using a polyclonal polyoma virus-reactive antibody. Urine samples (50 ml) were collected prior to biopsy by clean catch from the renal transplant recipients who had an elevated Cr of 20% or more above baseline and who were to undergo renal transplant biopsy as a diagnostic procedure. Patients with biopsy proven acute rejection were hospitalized, treated with anti-rejection therapy, and donated daily urinary samples until the rejection resolved. The collected samples were centrifuged at 1500 rpm for 10 min. The supernatant of each sample was aliquoted and stored at −80° C. until use. At the time of experiments, samples were thawed and evaluated for the levels of IP-10, Mig and I-TAC.

Quantification of Urinary IP-10, Mig and I-TAC

Luminex (Austin, Tex.) Multi-Analyte Profiling (xMAP) Technology and Renovar (Madison, Wis.) human CXCR3 binding chemokines triplex assay kits were used for quantification of urinary IP-10, Mig and I-TAC. Luminex xMAP is based on polystyrene particles (microspheres) that are internally labeled with 2 different fluorophores. When excited by a 635-nm laser, the fluorophores emit light at different wavelengths, 658 and 712 nm. By varying the 658-nm/712-nm emission ratios, the beads are individually classified by the unique Luminex 100 IS analyzer. A third fluorophore coupled to a reporter molecule allows for quantification of the interaction that has occurred on the microsphere surface. The capture antibodies directed respectively to IP-10, Mig and I-TAC were separately pre-conjugated to their corresponding particles following the Luminex coupling protocol. The quantification of CXCR3 binding chemokines was conducted in 96-well flat-bottom plates. Twenty-five μl of mixed IP-10, Mig and I-TAC standards or urinary samples were added to wells containing 25 μl of assay buffer and 25 μl of pre-coated particles, and incubated on a 3-D rotator (Labline Instrument Inc., Melrose Park, Ill.)

at 60 rounds/min at room temperature (RT) for 60 min. Mixed biotin labeled detection antibodies directed at IP-10 (BD PharMingen, San Jose, Calif.), Mig and I-TAC (R&D Systems, Minneapolis, Minn.) were then added and incubated on the rotator at 60 rounds/min at RT for 60 min before the addition of streptavidin-PE (BD PharMingen). After an additional 30 min incubation on the rotator at 60 rounds/min at RT, data acquisition and analysis were performed on a Luminex 100 IS analyzer.

Statistical Analysis

The levels of urinary IP-10, Mig and I-TAC were expressed as mean value±standard error (SE). The statistical significance of the findings was assessed by ANOVA using computer software Prism 4 from GraphPad Software (San Diego, Calif.), and a p value less than 0.05 was considered significant. The urinary chemokine threshold that gave the maximal sensitivity and specificity for the diagnosis of acute dysfunction of renal allograft was 100 pg/ml. Sensitivity, specificity, positive predictive value (PPV) and negative predictive value (NPV) of the urinary chemokine test was calculated as follows: sensitivity=number of true positive specimens (TP)/[TP+number of false negative specimens (FN)]; specificity=number of true negative specimens (TN)/[TN+number of false positive specimens (FP)]; PPV=TP/(TP+FP), and NPV=TN/(TN+FN).

Levels of Urinary Chemokines in Patients and Control Individuals

Figure 2:
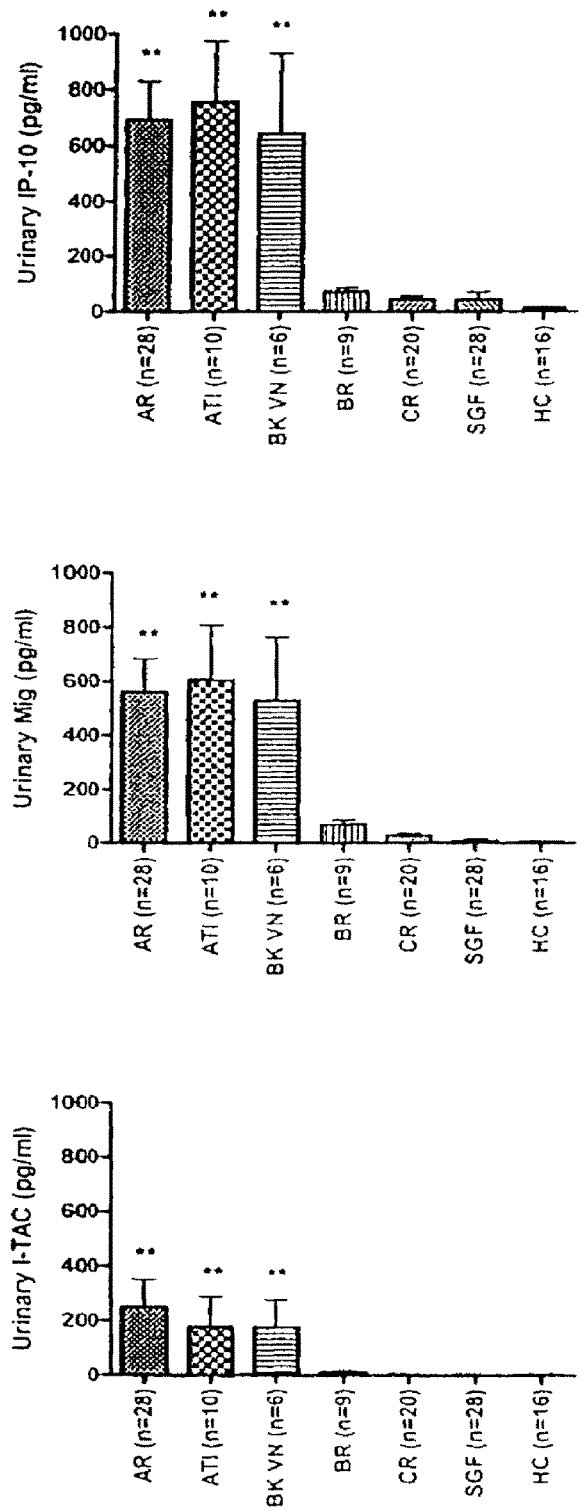
FIG. 2 shows urinary levels of CXCR3 binding chemokines IP-10, Mig and I-TAC in recipients of renal allografts, acute tubular injury, BK virus nephritis, borderline rejection, chronic rejection, stable graft function and healthy controls.

Urinary IP-10, Mig and I-TAC were simultaneously quantified in each urine sample by the Luminex xMAP method. FIG. 2 shows that urinary levels of CXCR3-binding chemokines IP-10, Mig and I-TAC were significantly elevated ($P<0.01$) in samples collected from recipients with acute rejection (AR), BK virus nephritis (BK VN), and acute tubular injury (ATI), but not in samples collected from recipients with borderline rejection (BR), chronic rejection (CR), and stable graft function (SGF). Furthermore, urinary samples collected from healthy control (HC) individuals contained very low levels of the measured chemokines (FIG. 2).

Urinary Chemokines as a Sensitive and Specific Indicator of Acute Renal Allograft Dysfunction After renal transplantation, graft dysfunction may occur due to treatable etiologies such as acute rejection, acute tubular injury, or BK virus nephritis. Other types of graft injury may occur more insidiously and usually do not require acute intervention, such as chronic rejection and recurrence of the original disease. Acute dysfunction refers herein to acute rejection, acute tubular injury and BK virus nephritis. Levels of urinary IP-10, Mig and I-TAC varied greatly among the study subjects, ranging from 0 pg/ml to 2000 pg/ml. Using 100 pg/ml as the cutoff level for the urinary chemokines that gave the maximal sensitivity and specificity, as presented in FIG. 3, most of the renal graft recipients with acute rejection, BK virus nephritis and acute tubular injury had higher levels of urinary IP-10 and Mig, while most of the recipients with chronic rejection and stable graft function had lower levels of urinary IP-10 and Mig (FIG. 3). For recipients with borderline rejection, 4 out of 9 cases showed higher levels. None of the healthy controls had urinary IP-10, Mig or I-TAC higher than 100 pg/ml. The elevation of urinary IP-10 and Mig was more prevalent than I-TAC in recipients with acute dysfunction caused by acute rejection, acute tubular injury and BK virus nephritis. As shown in FIG. 2 and FIG. 3, elevation of urinary IP-10 and Mig indicated acute renal injury by one of the three etiologies. To evaluate the value of urinary IP-10 and/or Mig to differentiate the acute dysfunction from chronic rejection and stable graft function, we calculated the sensitivity, specificity, positive predictive value and negative predictive value as presented in FIG. 4. Both IP-10 and Mig are highly sensitive and specific.

Urinary chemokine levels were compared to the renal function indicator, serum Cr. When urinary IP-10 was used in the analysis, most of the recipients with acute dysfunction had increased urinary IP-10 and serum Cr. Recipients with chronic rejection had increased Cr, but not IP-10. Recipients with stable graft function had low IP-10 and Cr levels.

Decline of Urinary Chemokines after Anti-rejection Therapy

Figure 5:
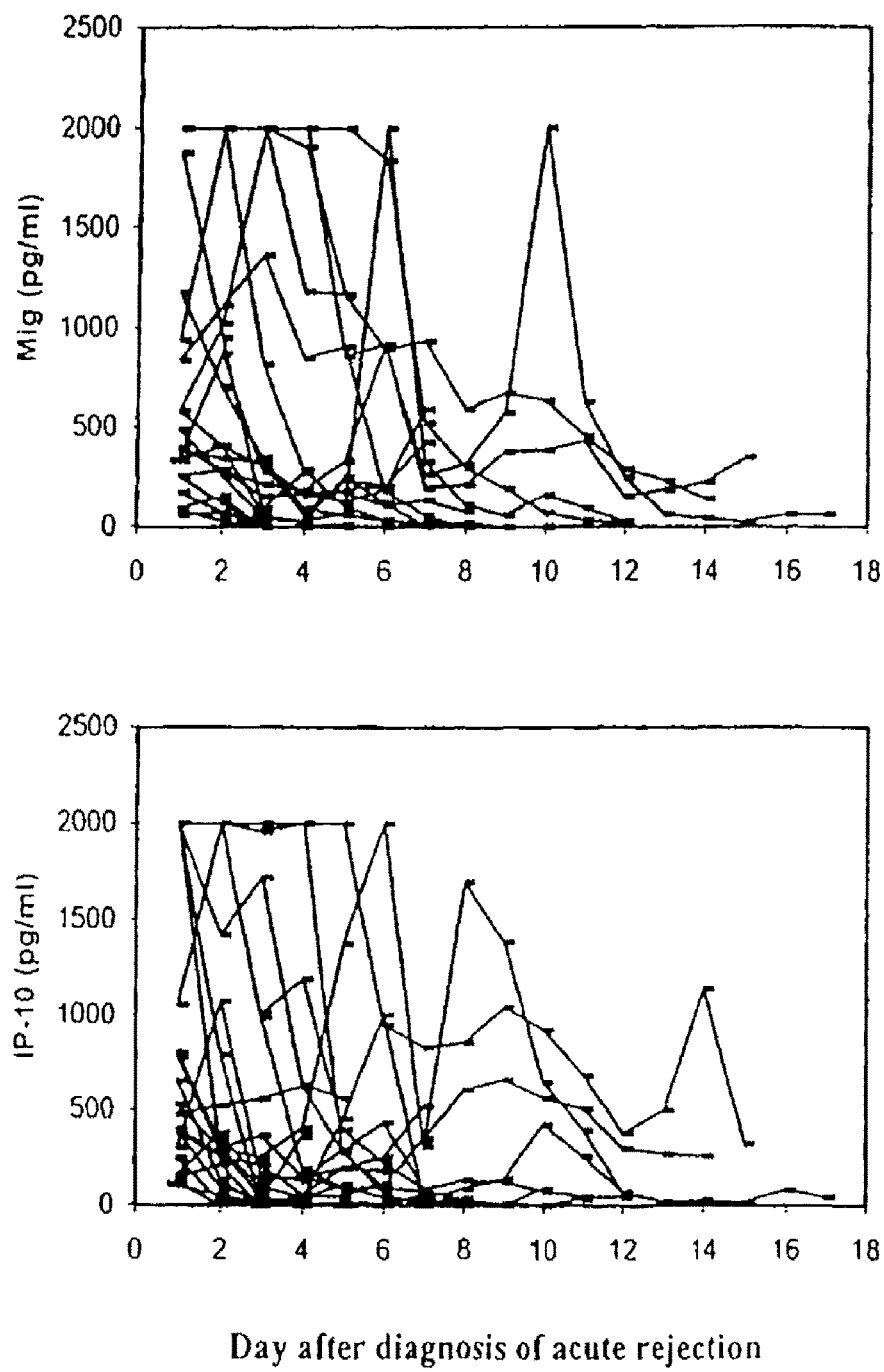
FIG. 5 shows the decline of urinary IP-10 and Mig in recipients with acute rejection after anti-rejection therapy.

Among the 28 patients with acute rejection, daily urinary samples were collected from 24 during hospitalization for anti-rejection therapy. Day 1 is the time that acute rejection was diagnosed and anti-rejection therapy was initiated. As presented in FIG. 5, urinary IP-10 and Mig declined with the initiation of anti-rejection therapy on day 1, and most of the recipients reached a level below 100 pg/ml in their last collected urinary sample.

Figure 6:
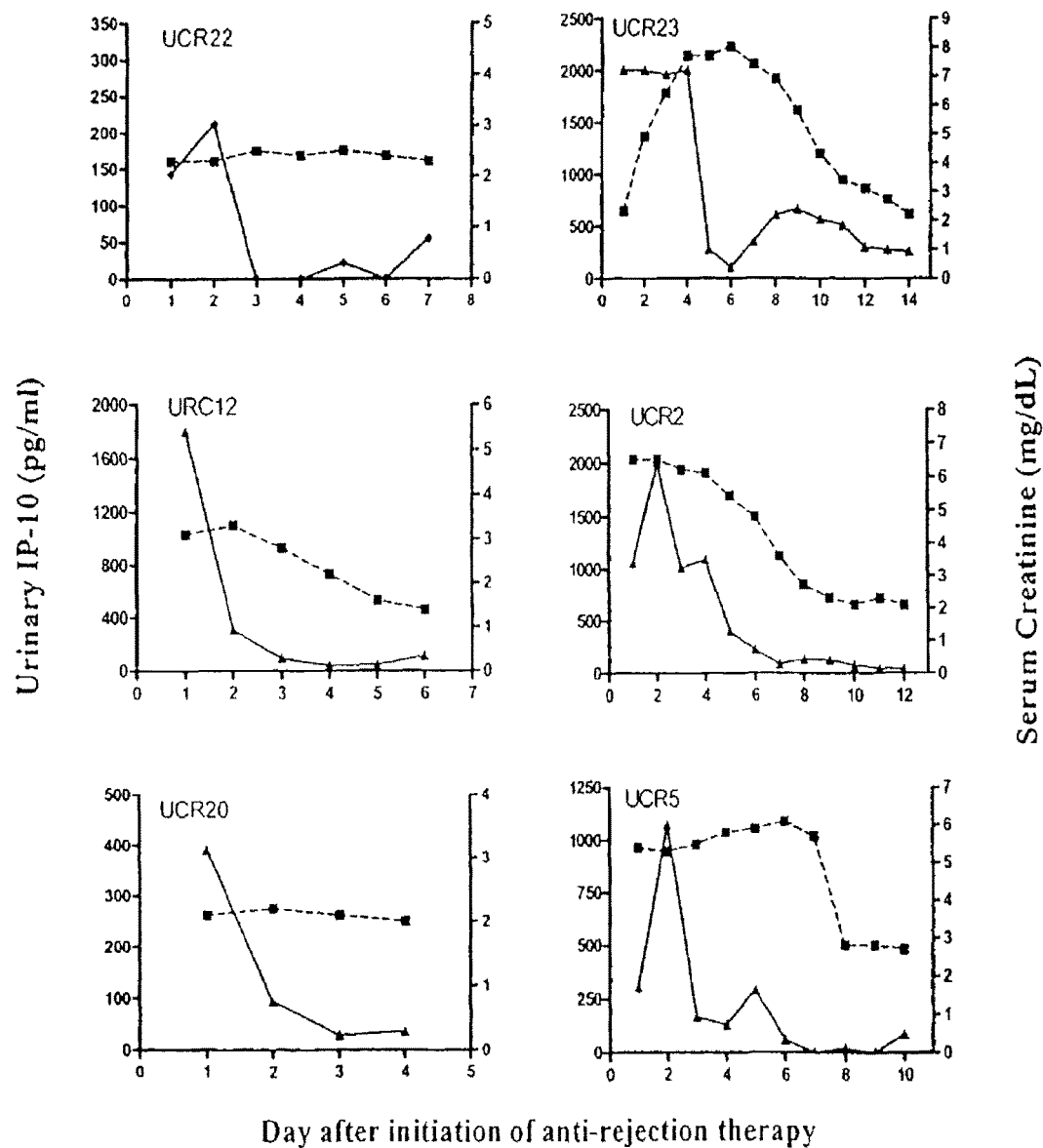
FIG. 6 shows that urinary IP-10 levels decline several days earlier than serum creatinine in acute rejection patients receiving anti-rejection therapy.

Serum Cr is an important parameter used to judge the effectiveness of anti-rejection therapy. Therefore, we compared the levels of serum Cr and urinary chemokines in the recipients who received anti-rejection therapy. As shown in FIG. 6, urinary IP-10 (solid triangle) declined several days earlier than serum creatinine (solid square) in acute rejection patients receiving anti-rejection therapy. Urinary and serum samples were collected once daily from each of the patients, and urinary IP-10 and serum Cr were separately determined. UCR2, UCR5, UCR23, and UCR 12 are representative patients that had elevated serum Cr initially which declined with anti-rejection therapy. UCR20 and UCR22 are representative patients that had elevated serum Cr initially, but Cr did not decline with anti-rejection therapy during the hospitalization period. Thus, as shown in FIG. 6, the serum Cr in the recipients who were hospitalized for 3-14 days could be classified into two patterns: started high and remained high for several days before declining (represented by UCR2, UCR5, UCR23, and UCR 12), or started at the lower range of the abnormal level and maintained that level (represented by UCR20 and UCR22) during the hospitalization. In contrast to serum Cr kinetics, urinary IP-10 declined in all patients, with this decrement starting 2-5 days earlier than the serum Cr (FIG. 6).

Example 5

Diagnosis of Kidney Disorders Using Levels of Urine Cytokine, Cytokine-Relate Compounds and Chemokines Subjects Renal transplant patients were recruited from the Transplant Clinic of the University of Wisconsin Hospital and Clinics. The research protocol was approved by the University of Wisconsin Institutional Review Board, and all patients provided informed consent. On the day of biopsy, urine samples (50 ml) were collected prior to biopsy by clean catch from patients who had an elevated serum creatinine (Cr) of 20% or more above baseline, and who were to undergo renal transplant biopsy as a diagnostic procedure. One hundred and thirteen renal allograft recipients were recruited. Among the patients, 37 were diagnosed as acute rejection (AR), 10 as borderline rejection, 4 as antibody-mediated acute rejection (ABAR), 4 as BK virus nephropathy (BKVN), 9 as acute tubular necrosis (ATN), 20 as chronic allograft nephropathy (CAN), and 29 as stable graft function. All patients except those with stable graft function had a biopsy and pathologic diagnosis. Urine samples were also collected from 19 healthy non-transplanted individuals.

The urine samples were centrifuged at 1500 rpm for 10 min. The supernatant of each sample was aliquoted and stored at −80° C. until use. At the time of experiments, the samples were thawed and evaluated. Patients with signs and symptoms of a kidney disorder and/or elevated serum Cr underwent renal transplant biopsy. Acute and chronic rejection was scored according to Banff criteria by an experienced renal transplant pathologist. BKVN was diagnosed by light-microscope via identification of pleomorphic, enlarged tubular epithelial cell nuclei containing characteristic "smudgy" inclusions. The diagnosis of BKVN was confirmed by immunohistochemistry using a polyclonal polyoma virus-reactive antibody.

Screening Urinary Samples with a Cytokine/Cytokine-Related Compound/Chemokine Array Three urinary samples from renal transplant recipients and 3 samples from healthy controls were used for the initial screening assay using RayBio® Human Cytokine Antibody Array C Series 1000 kit (RayBiotech, Norcross, Ga.). This antibody array detects and measures 120 cytokines, cytokine-related compounds and chemokines. The manufacturer's suggested experimental procedures were followed. Briefly, after blocking and washing the array membrane, 2 ml of urine sample were mixed with 2 ml of reaction buffer, and added onto the array membrane and incubated at 4° C. overnight. The reaction buffer is described in U.S. patent application Ser. No. 10/968,597, "Reagents for Urine-Based Immunological Assay", filed Oct. 19, 2004, which is incorporated herein by reference in its entirety. The array membrane was then washed 3 times, followed by incubation with the biotin labeled detection antibody mixture at room temperature (RT) for 2 hours. After washing, 2 ml of 1000 fold diluted HRP-conjugated streptavidin were applied to the array membrane and incubated at RT for 2 hours. Detection reagent was added to the array membrane after washing away the unbound HRP-conjugated streptavidin. Signal detection was done by exposing an X-ray film to the array membrane.

Figure 7:
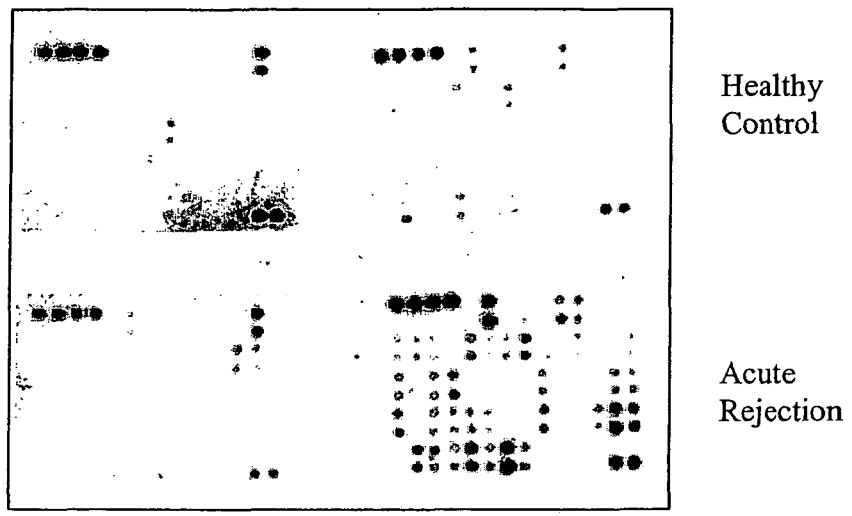
FIG. 7 shows that urine samples from recipients with acute renal graft rejection yield more positive signals for the presence of cytokines, cytokine-related compounds and chemokines, than samples of healthy individuals, indicating that transplanted kidneys undergoing acute rejection produce cytokines, cytokine-related proteins and chemokines that are lacking, or present at much lower levels, in the absence of acute rejection.
Figure 9:
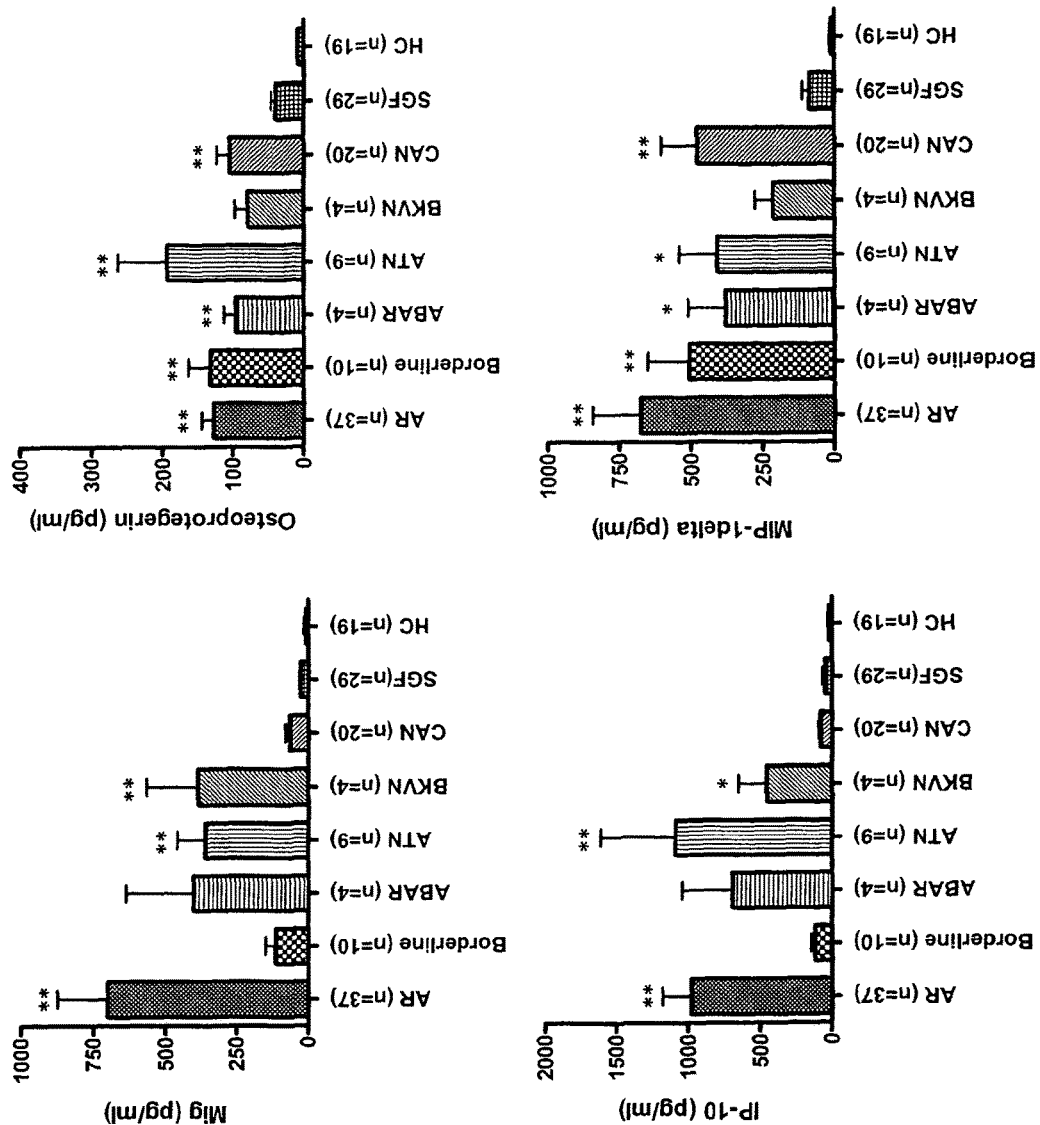
FIG. 9 shows that urine levels of IP-10 and Mig are significantly elevated in samples collected from recipients with acute graft rejection (AR), acute tubular necrosis (ATN) and BK viral nephropathy (BKVN), but not in samples collected from recipients with borderline rejection, antibody-mediated acute rejection (ABAR), chronic renal allograft rejection (CAN), or in patients with stable graft function (SGF). Urine samples collected from healthy individuals (HC) contain very low levels of IP-10 and Mig.
Figure 10:
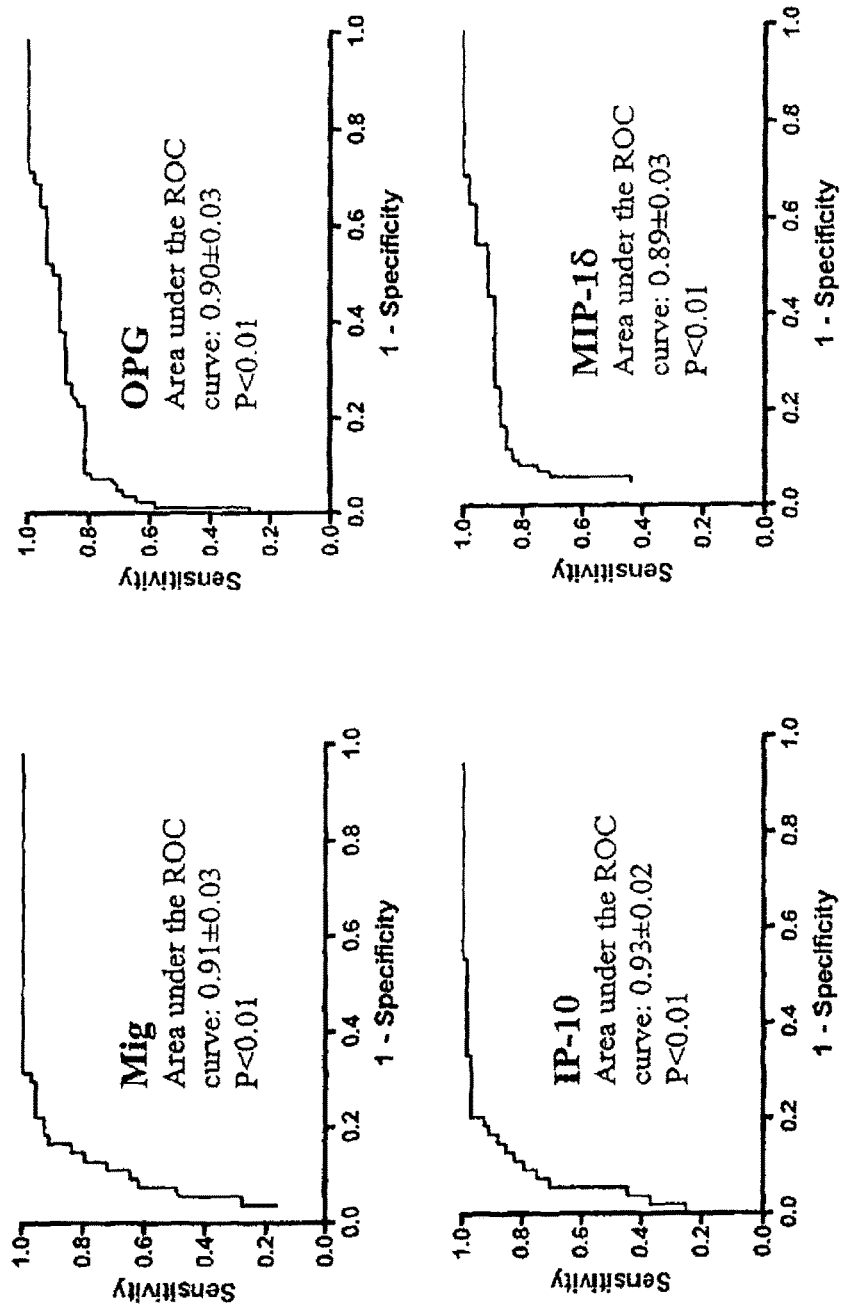
FIG. 10 shows that urine levels of IP-10 and Mig differentiate AR, ABAR, ATN and BKVN from CAN and stable graft function with high sensitivity and specificity as depicted in ROC curves.

Screening Urinary Samples with a Cytokine/Cytokine-Related Compound/Chemokine Array In experiments performed with the RayBio® Human Cytokine Antibody Array C Series 1000 kit, 23 cytokines, cytokine-related compounds or chemokines were found to have higher signals in the urinary samples derived from the renal graft rejection patients than in the samples of healthy controls (FIG. 7). Acute rejection (AR) is the most common acute complication after kidney transplantation, exhibiting severe inflammation mediated by immune reaction. As shown in FIG. 7, urine samples derived from kidney recipients with AR yield much more positive signals compared to the samples of healthy individuals, indicating that the transplanted kidneys with AR produce cytokines, cytokine-related compounds and chemokines that are not made or made much less by the healthy kidney. By comparing the screening results, 23 cytokines, cytokine-related compounds and chemokines that appeared with stronger signals in the AR urine samples were selected for further evaluation (FIG. 8). Besides these 23 cytokines, cytokine-related compounds and chemokines, Mig also presented a stronger signal in the AR samples. Because CXCR3 binding chemokines in urine samples of renal transplant recipients were previously validated, Mig and IP-10 were not specifically incorporated into the Example 6 screening assay, but were included in the multiplex (that is, quadraplex) assays (FIGS. 9, 10 and 11).

Example 6

Further Screening the Cytokine and Chemokine Markers in Urine by a Luminex Microarray In experiments performed with the RayBio® Human Cytokine Antibody Array C Series 1000 kit, 23 cytokines, cytokine-related compounds and chemokines were found with higher signal intensity in urine samples derived from kidney rejection patients than in the samples of healthy controls (FIG. 7). These 23 cytokines/chemokines were further screened using a microarray developed on the Luminex (Austin, Tex.) Multi-Analyte Profiling (xMAP) platform. The Luminex xMAP platform is based on polystyrene particles (microspheres) that are internally labeled with 2 different fluorophores. When excited by a 635-nm laser, the fluorophores emit light at two wavelengths, 658 and 712 nm. By varying the 658-nm/712-nm emission ratios, the beads can be individually classified by the unique Luminex 100 IS analyzer. A third fluorophore coupled to a reporter molecule allows for quantification of the interaction that has occurred on the microsphere surface.

Twenty-three capture antibodies directed separately at the 23 cytokines, cytokine-related compounds and chemokines (FIG. 8) were purchased from R&D Systems (R&D Systems, Minneapolis, Minn.), and were separately conjugated to 23 distinct Luminex beads following the manufacturer's bead conjugation protocol. After confirming that the conjugation was successful, the 23 types of conjugated beads were mixed at a 1:1 ratio for the microarray assay. The experiment was conducted on a 96-well plate. Twenty-five μl of urinary samples were added to wells containing 25 μl of assay buffer and 25 μl of the pre-coated beads, and incubated on a 3-D rotator (Labline Instrument Inc., Melrose Park, Ill.) at 60 rounds/min at RT for 60 min. The assay buffer is described in U.S. patent application Ser. No. 10/968,597, "Reagents for Urine-Based Immunological Assay", filed Oct. 19, 2004, which is incorporated herein by reference in its entirety. Mixed biotin labeled detection antibodies directed at the 23 cytokines/chemokines (R&D Systems, Minneapolis, Minn.) were then added and incubated on the rotator at 60 rounds/min at RT for 60 min. After vacuuming and washing, streptavidin-PE (BD PharMingen) (San Diego, Calif.) was added, and incubated on the rotator at 60 rounds/min at RT for 30 min. Data acquisition and analysis were performed on a Luminex 100 IS analyzer.

Quantification of Urinary IP-10, Mig, MIP-1δ and OPG

The Luminex xMAP Technology and Renovar human cytokine, cytokine-related compound and chemokines quadruplex assay kit (Madison, Wis.) were used for simultaneous quantification of urinary IP-10, Mig, MIP-1δ and OPG. The capture antibodies directed respectively at IP-10, Mig, MIP-1δ and OPG were separately pre-conjugated to their corresponding particles following the Luminex coupling protocol. Quantification of CXCR3 binding chemokines was conducted in 96-well flat-bottom plates. Twenty-five μl of mixed IP-10, Mig, MIP-1δ and OPG standards or urinary samples were added to wells containing 25 μl of assay buffer and 25 μl of pre-coated particles, and incubated on a 3-D rotator (Labline Instrument Inc., Melrose Park, Ill.) at 60 rounds/min at RT for 60 min. Mixed biotin labeled detection antibodies directed at IP-10 (BD PharMingen, San Jose, Calif.), Mig, MIP-1δ and OPG (R&D Systems, Minneapolis, Minn.) were then added and incubated on the rotator at 60 rounds/min at RT for 60 min before the addition of streptavidin-PE (BD PharMingen). After an additional 30 min incubation on the rotator at 60 rounds/min at RT, data acquisition and analysis were performed on a Luminex 100 IS analyzer.

Statistical Analysis

The levels of urinary IP-10, Mig, MIP-1δ and OPG were expressed as mean value ±standard error (SE). The statistical significance of the comparisons was assessed by ANOVA using computer software Prism 4 from GraphPad Software (San Diego, Calif.), and a p value less than 0.05 was considered significant. The urinary cytokine, cytokine-related compound or chemokine threshold that gave maximal sensitivity and specificity for the diagnosis of acute/chronic dysfunction of renal allograft was determined by using a receiver operation characteristics (ROC) curve. Sensitivity, specificity, positive predictive value (PPV) and negative predictive value (NPV) of the urine tests were calculated as follows: sensitivity=number of true positive specimens (TP)/[TP+number of false negative specimens (FN)]; specificity=number of true negative specimens (TN)/[TN+number of false positive specimens (FP)]; PPV=TP/(TP+FP), and NPV=TN/(TN+FN).

Further Screening the Cytokine and Chemokine Markers in Urine by a Luminex Microarray The Luminex xMAP array was chosen to further evaluate the 23 cytokines, cytokine-related compounds and chemokines derived from the RayBio® array assay. As shown in FIG. 8, multiple samples were obtained for classification of the 23 cytokines, cytokine-related compounds and chemokines into 3 groups. Group I includes angiogenin, TIMP-2, TNF sR2 and Trail R3. These factors are expressed at relatively high levels in urine samples from patients with AR, ATN, CAN and stable graft function, and from the healthy individuals. Group II includes IL-1β, IL-2sRα, IL-6, MIP-1α, MIP-1β, MIP-3α, IL-18, and TNF-α. These factors are expressed relatively low levels in urine samples from renal transplant recipients, and healthy individuals. Group III includes adiponectin, IGFBP-1, IGFBP-2, IGFBP-6, IL-8, leptin, MCP-1, MIP-1δ, TNF sR1, osteoprotogerin (OPG), and uPAR. These markers are expressed at higher levels in urine samples from renal transplant recipients with AR, ATN, and CAN than in urine samples derived from kidney recipients with stable graft function, and from healthy individuals.

Levels of Urinary IP-10, Mig, MIP-1δ and OPG in Patients and Control Individuals After two rounds of screening assays, adiponectin, IGFBP-1, IGFBP-2, IGFBP-6, leptin, MIP-1δ, OPG, and uPAR exhibited the highest correlation with the diagnosis of kidney disorders. For a more detailed evaluation, a quadruplex Luminex xMAP assay including IP-10, Mig, MIP-1δ and OPG was developed. This quadruplex Luminex xMAP assay simultaneously measures the concentration of IP-10, Mig, MIP-1δ and OPG in urine. As shown in FIG. 9, urine IP-10 and Mig are significantly elevated in samples collected from recipients with AR, BKVN, and ATN, but not in samples collected from recipients with borderline rejection, ABAR, chronic rejection, and stable graft function. Urine samples collected from healthy individuals contained very low levels of IP-10 and Mig. MIP-1δ and OPG were significantly elevated in samples collected from kidney recipients with AR, borderline rejection, ABAR, ATN, and CAN, but not in samples collected from recipients with stable graft function and healthy individuals.

Urine IP-10, Mig, MIP-1δ and OPG as Indices of Renal Allograft Dysfunction

Acute graft dysfunction after transplant may arise from diverse etiologies, for example, AR, ATN, or BK viral nephropathy. Urgent and specific intervention tailored to each diagnosis is often required. Other types of graft injury, for example borderline rejection and CAN at early stage, may be insidious. The latter cases may not require urgent treatment, but early intervention (for instance, discontinue renal-toxic immunosuppressive agents and treat borderline rejection) may protect the graft from further damage. Early detection and specific diagnosis of these kidney disorders is therefore essential to the protection of the renal grafts and their recipients.

The present data shows that the quadraplex assays of the present invention have the capacity to detect, identify and differentiate acute and chronic kidney disorders. As depicted in ROC curves, urine IP-10 and Mig demonstrate sensitivity and specificity sufficient to distinguish AR, ABAR, ATN and BKVN from CAN and stable graft function (FIG. 10). In turn, urine MIP-1δ and OPG demonstrate sensitivity and specificity sufficient to discriminate AR, ABAR, ATN, BKVN, borderline rejection and CAN from stable graft function. While absolute urine levels of IP-10, Mig, MIP-1δ and OPG vary from subject to subject, using 80 pg/ml as a cutoff level for each of the markers provides maximal sensitivity and specificity (FIG. 11). With this threshold, the majority of renal transplant recipients with AR, ABAR, ATN and BKVN have high levels of IP-10 and Mig, whereas most of recipients with CAN and stable graft function express urine levels of IP-10 and Mig beneath than the cutoff. While MIP-1δ and OPG may overlap with IP-10 and Mig in detection of acute injuries caused by AR, ABAR, ATN and BKVN, both are strongly positive in urine samples from recipients with borderline rejection and CAN. To the contrary, the majority of kidney recipients with stable graft function have a level below the cutoff. One individual in the healthy controls showed a higher level than the cutoff for IP-10 and Mig. Using the 4 biomarkers in aggregate to detect and diagnose kidney injuries, including both acute and chronic injuries (AR, ABAR, ATN, BKVN, borderline rejection, and CAN), among the 84 patients that had renal allograft injuries only 2 cases (1 AR and 1 ATN) were negative for all the 4 parameters, while for the remaining 82 patients at least 1 of the 4 parameters was positive. These results indicate that use of the current panel of the present invention to detect kidney disorders provides a very high positive detection rate (97.6%).

The diagnostic value of the quadruplex assay of the present invention was further evaluated by calculation of indices of sensitivity, specificity, positive predictive value and negative predictive value (FIG. 12). IP-10 and Mig levels are both highly sensitive and highly specific to differentiate acute injury (AR, ABAR, ATN and BKVN) from CAN, stable graft function and healthy renal function. MIP-1δ and OPG are both highly sensitive and highly specific to differentiate acute injury (AR, ABAR, ATN and BKVN), borderline rejection and CAN from stable graft function and healthy renal function.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A mixture comprising:
   a) a urine sample from a subject having acute graft rejection, borderline rejection, acute tubular necrosis, or BK viral neuropathy; and
   b) immunoassay reagents that specifically bind to and detect IP-10.

2. The mixture of claim 1, wherein said mixture further comprises immunoassay reagents that specifically bind to and detect MIG.

3. The mixture of claim 1, wherein said mixture further comprises immunoassay reagents that specifically bind to and detect osteoprotogerin.

4. The mixture of claim 1, wherein said immunoassay reagents comprise antibodies.

5. The mixture of claim 1, wherein the urine sample was obtained from a subject that had an organ transplant.

6. The mixture of claim 1, wherein IP-10 is present at a concentration of 80 pg/ml or higher in said urine.

7. The mixture of claim 4, wherein said reagents further comprise beads.

* * * * *